(12) United States Patent
Kan

(10) Patent No.: US 9,932,597 B2
(45) Date of Patent: Apr. 3, 2018

(54) VECTORS FOR TRANSGENE EXPRESSION

(71) Applicant: Adaptimmune Limited, Abingdon, Oxford (GB)

(72) Inventor: On Kan, Oxford (GB)

(73) Assignee: ADAPTIMMUNE LIMITED, Abingdon, Oxford (GB)

(*) Notice: Subject to any disclaimer, the term of this patent is extended or adjusted under 35 U.S.C. 154(b) by 0 days.

(21) Appl. No.: 14/523,218

(22) Filed: Oct. 24, 2014

(65) Prior Publication Data

US 2015/0118714 A1    Apr. 30, 2015

Related U.S. Application Data

(60) Provisional application No. 61/189,994, filed on Oct. 24, 2013.

(30) Foreign Application Priority Data

Oct. 24, 2013  (GB) ..................... 1318804

(51) Int. Cl.
*C12N 15/67* (2006.01)
*C12N 15/86* (2006.01)

(52) U.S. Cl.
CPC ............. *C12N 15/67* (2013.01); *C12N 15/86* (2013.01); *C12N 2740/10043* (2013.01); *C12N 2740/15041* (2013.01); *C12N 2740/15043* (2013.01); *C12N 2799/027* (2013.01); *C12N 2830/38* (2013.01); *C12N 2830/48* (2013.01)

(58) Field of Classification Search
None
See application file for complete search history.

(56) References Cited

U.S. PATENT DOCUMENTS 7,629,153 B2 * 12/2009 Trono et al. ............... 435/91.4

FOREIGN PATENT DOCUMENTS

| EP | 1757702 A | 2/2007 |
|---|---|---|
| WO | WO02/064805 A | 8/2002 |
| WO | WO2005/056057 A | 6/2005 |
| WO | WO 2012/170911 | 12/2012 |

OTHER PUBLICATIONS

Ramenzani et al., Molecular Therapy, 2000, vol. 2 pp. 458-469.*
Parks et al, Journal of Virology, 1999, vol. 73, pp. 8027-8034.*
Hagen et al., Journal of Virology, 1994, vol. 68, pp. 1509-1515.*
Search report of UK Application No. GB1318804.0 dated Jul. 8, 2014.
Molecular Therapy, vol. 2, 2000, A Ramezani et al, "Lentiviral vectors for enhanced gene expression in human hematopoietic cells", 458-469.
Gene Therapy, vol. 20, 2013, JM Johnston et al, "Generation of an optimized lentiviral vector encoding a high-expression factor VIII for gene therapy of hemophilia A", 607-615.
Applied Microbiology and Biotechnology, vol. 91, 2011, G Real et al, "Improvement of lentiviral transfer vectors using cis-acting . . . ", 1581-1591.
Gene Therapy, vol. 11, 2004, M Werner et al, "B-cell-specific transgene expression using a self-inactivating retroviral vector . . . ", 992-1000.
Human Gene Therapy, vol. 14, 2003, BEngels et al, "Retroviral vectors for high-level transgene expression in T lymphocytes", 1155-1168.
International Search Report and Written Opinion of PCT Application No. PCT/EP2014/072852.
Dupuy F P et al: Lentiviral transduction of human hematopoietic cells by HIV-1- and SIV-based vectors containing a bicistronic cassette driven by various internal promoters, The Journal of Gene Medicine vol. 7 No. 9, Sep. 1, 2005 (Sep. 1, 2005) pp. 1158-1171.
Zanta-Boussif M A et al: Validation of a mutated PRE sequence allowing high and sustained transgene expression while abrogating WHV-X protein synthesis: application to the gene therapy of WAS, Gene Therapy, vol. 16 No. 5 May 1, 2009 (May 1, 2009), pp. 605-619.

* cited by examiner

*Primary Examiner* — Antonio Galisteo Gonzalez
(74) *Attorney, Agent, or Firm* — Vedder Price P.C.; Thomas J. Kowalski; Deborah L. Lu

(57) ABSTRACT

The present invention relates to a vector system involving replacement of a Woodchuck Hepatitis Virus Post-Transcriptional Regulatory Element (WPRE) sequence with an unrelated short spacer sequence for efficient expression of nucleotides of interest in a retroviral vector system and methods of delivering and expressing nucleotides of interest to target cells.

21 Claims, 12 Drawing Sheets

VECTORS FOR TRANSGENE EXPRESSION

RELATED APPLICATIONS AND/OR INCORPORATION BY REFERENCE

This application is claims benefit of and priority to U.S. provisional patent application Ser. No. 61/894,994 filed Oct. 24, 2013, UK patent application Serial No. GB1318804.0 filed Oct. 24, 2013 and international patent application Serial No. PCT/EP2014/072852 filed Oct. 24, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a vector system which may comprise a spacer or stuffer nucleotide sequence (SNS) in place of a post-transcriptional regulatory element. In particular, the present invention relates to the replacement of a Woodchuck Hepatitis Virus Post-Transcriptional Regulatory Element (WPRE) sequence with an unrelated short spacer sequence which facilitates the efficient expression of nucleotides of interest in a retroviral vector system. The present invention also relates to methods of delivering and expressing nucleotides of interest to target cells.

BACKGROUND OF THE INVENTION

Retroviral vector systems, such as lentiviral vector systems, have been proposed as a delivery system. WO98/17815 relates to the removal of many of the accessory genes. WO99/45126 relates to codon optimisation of the gag-pol sequence as a means of seeking to overcome the Rev/RRE requirement for export and to enhance RNA stability The hepatitis B virus (HBV) post-transcriptional regulatory element (PRE) and an intron may be functionally equivalent [Huang, Z. M. and Yen, T. S. (1995) Mol. Cell. Biol. 15: 3864-386]). Woodchuck hepatitis virus (WHV), a close relative of HBV, also harbors a PRE (hereinafter referred to as WPRE; see U.S. Pat. No. 6,136,597 and U.S. Pat. No. 6,287,814). Insertion of the WPRE in lentiviral vectors resulted in significant enhancement of expression of reporter genes such as luciferase and green fluorescent protein (GFP) in a variety of cells spanning different species [Zufferey, R. et al, (1999) J. Virol 73: 2886-2892]. Stimulation was irrespective of the cycling status of transduced cells.

The WPRE contains three cis-acting sequences important for its function in enhancing expression levels. However, in addition, it contains a fragment of approximately 180 base pairs (bp), which may comprise the 5' end of the WHV X protein open reading frame, together with its associated promoter. The full-length X protein has been implicated in tumorigenesis [Flajolet, M. et al, (1998) J. Virol. 72: 6175-6180]. This has been directly demonstrated [U.S. Pat. No. 7,419,829] by administration of EIAV vector to fetal mice in utero: mice transduced with vectors containing the wild type EIAV developed liver tumors whereas mice transduced with vectors lacking the WPRE did not develop liver tumors. The tumorigenic activity of Cis-activation of myc family oncogenes due to the insertion of viral DNA into the host genome is known to be a key mechanism of WHV-mediated carcinogenesis (Buendia, M. A. (1994) In C. Brechot (ed.), Primary liver cancer: etiological and progression factors, p. 211-224; CRC Press, Boca Raton, Fla.; Fourel, G. (1994) In F. Tronche and M. Yaniv (ed.), Liver gene expression, p. 297-343; R. G. Landes Company, Austin, Tex.). Furthermore, in human hepatocellular carcinoma, hepatitis B virus X protein truncated at the C-terminal may be more oncogenic than the full length X protein (Tu H et al. 2001 Biological impact of natural COOH-terminal deletions of hepatitis B virus X protein in hepatocellular carcinoma tissues. Cancer Res 61: 7803-7810).

U.S. Pat. No. 7,419,829 involves the replacement of the wildtype WPRE sequence with a mutant WPRE sequence designed to maintain the enhanced transgene expression without expression of the X-protein. It is believed that there are a limited number of changes that may be made to the WPRE without affecting its ability to enhance transgene expression. However, it is known that retroviral reverse transcriptases have low fidelity (an average single mistake incorporated per 10,000 nucleotides reverse transcribed) The possibility remains therefore for any mutated WPRE to revert to a functional wild-type sequence with tumorigenic potential.

Real et al (Appl Microbiol Biotechnol [2011]91:1581) shows that the removal of WPRE in a lentiviral vector significantly decreases transgene expression, as does Ramezani et al (Molecular Therapy [2000]2(5):458). Johnson et al (Gene Therapy [2013]20:607) showed that in a lentiviral system where the transgene is already optimised for high expression, removal of the WPRE has no significant effect on transgene expression: they are however silent on the replacement of the WPRE with a stuffer sequence. EP1757702 describes a gamma-retroviral vector system which can support high transgene expression in the absence of a WPRE: again this is silent on replacement of the WPRE with a stuffer sequence.

Citation or identification of any document in this application is not an admission that such document is available as prior art to the present invention.

SUMMARY OF THE INVENTION

The present inventors have now surprisingly shown that replacement of the WPRE by a short unrelated nucleotide sequence promotes enhanced expression levels of heterologous genes or nucleotides of interest from retroviral and lentiviral expression vectors. Thus total removal of the ORF of the X-protein removes the tumorigenic potential of this sequence increasing the safety profile for therapeutic use of these vectors.

According to a first aspect of the present invention, there is provided an engineered nucleic acid molecule lacking a woodchuck hepatitis virus post-transcriptional regulatory element (WPRE), wherein a spacer nucleotide sequence is inserted in place of the WPRE. In a preferred embodiment, the isolated nucleic acid molecule may comprise the sequence of SEQ ID NO: 1 [TCTAGA]. The WPRE may contain an X region In a second aspect of the present invention, a retroviral vector genome which may comprise at least one nucleotide sequence of interest (NOI) and the isolated nucleic acid molecule according to the first aspect of the invention is provided.

Preferably, the retroviral vector genome may be a lentiviral vector genome. Particularly, the lentiviral vector genome may be a minimal lentiviral vector genome. The lentiviral vector genome may be derived from a viral species selected from the group consisting of human immunodeficiency virus (HIV), simian immunodeficiency virus (SIV), visnalmaedi virus (VMV), caprine arthritis-encephalitis virus (CAEV), equine infectious anaemia virus (EIAV), feline immunodeficiency virus (FIV), and bovine immunodeficiency virus (BIV).

In another preferred embodiment, a nucleic acid sequence encoding Rev, or a functional equivalent thereof, may be disrupted such that the nucleic acid sequence is incapable of encoding the functional Rev or is removed from the vector genome.

In yet another preferred embodiment, a nucleic acid sequence encoding Tat may be disrupted such that the nucleic acid sequence is incapable of encoding functional Tat or is removed from the vector genome.

A preferred embodiment of the present invention provides a retroviral vector genome that may comprise a central polypurine tract (cPPT) sequence. In another preferred embodiment, the retroviral vector genome may comprise a gag-packaging signal having ATG motifs, and wherein the ATG motifs may be ATTG motifs.

In another preferred embodiment, the retroviral vector genome may be multicistronic and may comprise at least one internal regulatory element. Preferably, the internal regulatory element may be a promoter or an internal ribosomal entry site (IRES).

According to a third aspect of the present invention, there is provided a retroviral vector system for producing a retrovirus-derived vector particle, which may comprise (i) the retroviral vector genome according to the second aspect of the invention, (ii) a nucleotide sequence encoding retroviral gag and pol proteins; (iii) nucleotide sequences encoding other essential viral packaging components not encoded by the nucleotide sequence of (ii). Preferably, nucleic acid sequence(s) encoding at least one of Vpr, Vif, Tat, Nef, or analogous auxiliary genes, from the retrovirus from which the particles are derived, may be disrupted such as said nucleic acid sequence(s) are incapable of encoding functional Vpr, Vif, Tat, Nef, or analogous auxiliary proteins, or are removed from the system.

Preferably, the vector system may be pseudotyped with at least part of a heterologous env protein. In particular, the heterologous env protein may be derivable from Rabies-G or VSV-G.

In a fifth aspect of the invention, a viral particle produced from the retroviral vector system of the present invention is provided.

A sixth aspect of the invention provides a cell that has been transduced with the retroviral vector system of the present invention.

In a seventh aspect of the invention, a composition which may comprise the retroviral vector genome of the present invention, together with a carrier or a diluent, is provided.

An eighth aspect of the invention provides a composition which may comprise a viral particle of the present invention, together with a carrier or a diluent.

A ninth aspect of the invention provides a method of delivering at least one NOI to a target cell, which may comprise introducing the retroviral vector genome of the present invention into the target cell, whereby the NOI is delivered to the target cell.

A further aspect of the invention provides the spacer or stuffer sequences as provided herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
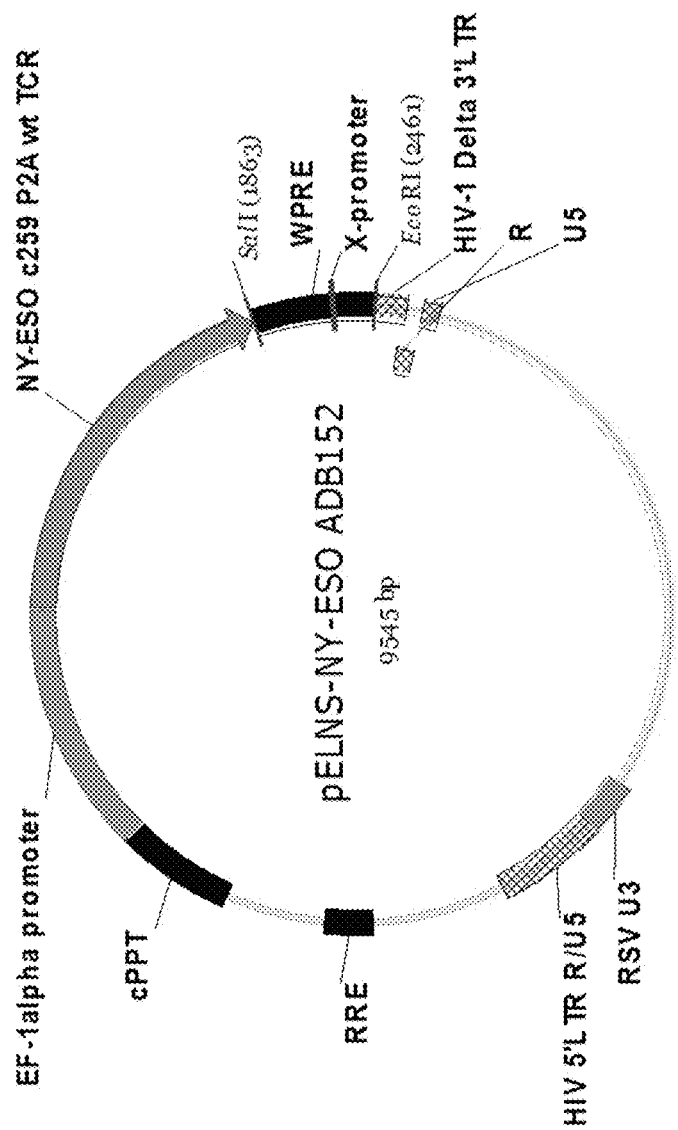
FIG. 1 is a schematic map of the original transfer plasmid designated pELNS-NY-ESO ADB152.

Various preferred features and embodiments of the present invention will now be described by way of non-limiting examples. Although in general, the techniques mentioned herein are well known in the art, reference may be made in particular to Sambrook, et al., Molecular Cloning, A Laboratory Manual (1989) and Ausubel et al., Short Protocols in Molecular Biology (1999) 4$^{th}$ Ed., John Wiley & Sons, Inc. (as well as the complete version of Current Protocols in Molecular Biology).

As used herein, the term "operably linked" means that the components described are in a relationship permitting them to function in their intended manner.

The Woodchuck hepatitis virus (WHV) post-transcriptional regulatory element (WPRE) may enhance expression from a number of different vector types including lentiviral vectors [U.S. Pat. Nos. 6,136,597; 6,287,814; Zufferey, R., et al. (1999) J. Virol. 73: 2886-92]. Without wanting to be bound by theory, this enhancement is thought to be due to improved RNA processing at the post-transcriptional level, resulting in increased levels of nuclear transcripts. A twofold increase in mRNA stability also contributes to this enhancement [Zufferey, R., et al. ibid]. The level of enhancement of protein expression from transcripts containing the WPRE versus those without the WPRE has been reported to be around 2-to-5 fold, and correlates well with the increase in transcript levels. This has been demonstrated with a number of different transgenes (Zufferey, R., et al. ibid).

The WPRE contains three cis-acting sequences important for its function in enhancing expression levels. In addition, it contains a fragment of approximately 180 bp which may comprise the 5'-end of the WHV X protein ORF (full length ORF is 425 bp), together with its associated promoter. Translation from transcripts initiated from the X promoter results in formation of a protein representing the NH$_2$-terminal 60 amino acids of the X protein. This truncated X protein may promote tumorigenesis, particularly if the truncated X protein sequence is integrated into the host cell genome at specific loci [Balsano, C. et al, (1991) Biochem. Biophys Res. Commun. 176: 985-92; Flajolet, M. et al, (1998) J. Virol. 72: 6175-80; Zheng, Y. W., et al, (1994) J. Biol. Chem. 269: 22593-8; Runkel, L., et al, (1993) Virology 197: 529-36]. Furthermore, X protein truncated at the C-terminal may be more oncogenic than the full length X protein (Tu H et al. 2001 Cancer Res 61: 7803-7810). Therefore, expression of the truncated X protein could promote tumorigenesis if delivered to cells of interest, precluding safe use of wild-type WPRE sequences.

As used herein, the "X region" of the WPRE is defined as having at least the first 60-amino acids of the X protein ORF, including the translation initiation codon, and its associated promoter. A "functional" X protein is defined herein as a truncated X protein that is capable of promoting tumorigenesis, or a transformed phenotype, when expressed in cells of interest. A "non-functional" X protein in the context of this application is defined as an X protein that is incapable of promoting tumorigenesis in cells of interest.

The present inventor has replaced the WPRE sequence with a spacer or stuffer nucleotide sequence (SNS) and found that efficient transcription still occurs: thereby the possibilty of tumorigenesis mediated by the X-protein ORF is prevented. The spacer or stuffer nucleotide sequence (SNS) may be any sequence that is advantageously a sequence other than a WPRE sequence that is random and/or non-coding and advantageously does not contain a start codon. Preferably, the stuffer also contains restriction enzyme sites for restriction enzymes that cut infrequently (i.e., that are unlikely to be present in the nucleic acid being analyzed) and are not present in the multiple cloning region of the library vector to permit removal of multiple stuffer sequences.

Thus, the invention provides an engineered or non-naturally occurring retroviral vector which may comprise a spacer or stuffer nucleotide sequence (SNS) inserted downstream from a nucleotide sequence of interest (NOI), wherein the SNS is heterologous to the vector and does not include a stop codon, and wherein the vector does not contain a woodchuck hepatitis virus post-transcriptional regulation element (WPRE). The SNS may be immediately downstream of the NOI sequence. In other words, the invention provides an engineered or non-naturally occurring retroviral vector in which the WPRE has been replaced by an SNS.

Advantageously, the spacer or stuffer nucleotide sequence (SNS) is about 3 nucleotides, about 4 nucleotides, about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, or about 50 nucleotides.

In another embodiment, the spacer or stuffer nucleotide sequence (SNS) may be about 3 to 50 nucleotides, about 5 to 45 nucleotides, about 7 to 40 nucleotides, about 10 to 30 nucleotides or about 15 to 25 nucleotides. In a particularly advantageous embodiment, the spacer or stuffer nucleotide sequence (SNS) may be about 3 to 20 nucleotides, about 3 to 18 nucleotides, about 3 to 16 nucleotides, about 3 to 14 nucleotides, about 3 to 12 nucleotides, about 3 to 10 nucleotides, about 3 to 9 nucleotides, about 3 to 8 nucleotides, about 3 to 7 nucleotides or about 3 to 5 nucleotides. The SNS may be from 50 to 200 nucleotides, from 75 to 175 nucleotides or from 100 to 150 nucleotides in length.

Preferably, this spacer or stuffer nucleotide sequence (SNS) is fewer than 10 nucleotides. The spacer or stuffer sequences form a further aspect of the invention.

The concept of using viral vectors for gene therapy is known (Verma and Somia (1997) Nature 389:239-242).

There are many retroviruses. For the present application, the term "retrovirus" includes: murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbor Laboratory Press Eds: J M Coffin, S M Hughes, H E Varmus pp 758-763).

Lentiviruses also belong to the retrovirus family, but they may infect both dividing and non-dividing cells [Lewis et al (1992) EMBO J. 3053-3058].

The lentivirus group may be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found in the HIV databases maintained by Los Alamos National Laboratory. Details of EIAV clones may be found at the NCBI database maintained by the National Institutes of Health. Also see U.S. Pat. Nos. 7,790,419; 7,585,676; 7,419,829; 7,351,585; 7,303,910; 7,198,784; 7,070,994; 6,924,123; 6,818,209; 6,808,922; 6,800.281; 6,783,981; 6,541,248; 6,312,683; and 6,312,682.

During the process of infection, a retrovirus initially attaches to a specific cell surface receptor. On entry into the susceptible host cell, the retroviral RNA genome is then copied to DNA by the virally encoded reverse transcriptase, which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which may leave the cell by a process sometimes called "budding".

Each retroviral genome may comprise genes called gag, pol and env, which code for virion proteins and enzymes. These genes are flanked at both ends by regions called long terminal repeats (LTRs). The LTRs are responsible for proviral integration, and transcription. They also serve as enhancer-promoter sequences. In other words, the LTRs may control the expression of the viral genes. Encapsidation of the retroviral RNAs occurs by virtue of a psi sequence located at the 5' end of the viral genome.

The LTRs themselves are identical sequences that may be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements may vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves; gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes, which code for proteins other than gag, pol and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Retroviral vector systems have been proposed as a delivery system for, inter alia, the transfer of a NOI to one or more sites of interest. The transfer may occur in vitro, ex vivo, in vivo, or combinations thereof.

A recombinant retroviral vector particle is capable of transducing a recipient cell with an NOI. Once within the cell, the RNA genome from the vector particle is reverse transcribed into DNA and integrated into the DNA of the recipient cell.

As used herein, the term "vector genome" refers to the RNA construct present in the retroviral vector particle and/or the integrated DNA construct. The term also embraces a separate or isolated DNA construct capable of encoding such an RNA genome. A retroviral or lentiviral genome may comprise at least one component part derivable from a retrovirus or a lentivirus. The term "derivable" is used in its normal sense as meaning a nucleotide sequence or a part thereof, which need not necessarily be obtained from a virus such as a lentivirus but instead could be derived therefrom. By way of example, the sequence may be prepared synthetically or by use of recombinant DNA techniques. Preferably the genome may comprise a psi region (or an analogous component that is capable of causing encapsidation).

The viral vector genome is preferably "replication defective", wherein the genome does not comprise sufficient genetic information alone to enable independent replication to produce infectious viral particles within the recipient cell. In a preferred embodiment, the genome lacks a functional env, gag or pol gene.

The viral vector genome may comprise some or all of the long terminal repeats (LTRs). Preferably the genome may comprise at least part of the LTRs or an analogous sequence, which is capable of mediating proviral integration, and transcription. The sequence may also comprise or act as an enhancer-promoter sequence.

The viral vector genome of the second aspect of the invention may be provided as a kit of parts. For example, the kit may comprise (i) a plasmid or plasmids containing the NOIs and internal regulatory sequences, such as, for example, a promoter or an IRES sequence(s); and (ii) a retroviral genome construct with suitable restriction enzyme recognition sites for cloning the NOIs and internal regulatory sequence(s) into the viral genome.

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell (see below).

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome having a psi region is introduced into the packaging cell line, the helper proteins may package the psi-positive recombinant vector RNA to produce the recombinant virus stock. This may be used to transduce the NOI into recipient cells. The recombinant virus whose genome lacks all genes required to make viral proteins may infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line which may comprise a viral vector genome of the present invention. For example, the packaging cell line may be transduced with a viral vector system which may comprise the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection [Landau & Littman (1992) J Virol 66:8 5110-5113; Pear et al (1993) Proc natl Acad Sci USA 90:18 8392-6]. The triple transfection procedure has been optimised (Soneoka et al Nucleic Acids Res (1995) 23:4 628-633; Finer et al (1994) Blood 83:43-50]. WO 94/29438 describes the production of producer cells in vitro using this multiple DNA transient transfection method.

The components of the viral system, which are required to complement the vector genome, may be present on one or more "producer plasmids" for transfecting into cells.

The present invention also provides a method of a reducing tumorgenicity associated with a retroviral vector which may comprise a WPRE containing an X region, the method which may comprise replacing the WPRE containing an X region with a spacer or stuffer nucleotide sequence (SNS).

The SNS may be as defined herein.

The replacement of the WPRE containing the X region with an SNS surprisingly results in reducing the tumorgenicity effect of the vector when transfected into cells but retaining the high fidelity of replication and efficiently enhanced transgene replication. The safety profile of such a retroviral vector is therefore increased over that of a vector containing the WPRE/X region sequences.

The present invention also provides a vector system for producing a retrovirus-derived particle, which may comprise (i) a retroviral genome according to the second aspect of the invention; (ii) a nucleotide sequence coding for retroviral gag and pol proteins; (iii) nucleotide sequences encoding other essential viral packaging components not encoded by the nucleotide sequence of (ii).

Preferably, the nucleic acid sequence(s) encoding at least one of Vpr, Vif, Tat, Nef, or analogous auxiliary genes, from the retrovirus from which the particles are derived, are disrupted such as said nucleic acid sequence(s) are incapable of encoding functional Vpr, Vif, Tat, Nef, or analogous auxiliary proteins, or are removed from the system.

The present invention also provides a cell transfected with such a vector system and a retroviral vector particle produced by such a cell. Preferably the gag-pol sequence is codon optimised for use in the particular producer cell (see below).

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts that may be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasmids. By cotransfection of the genome together with the producer plasmid(s), the necessary components should be provided for the production of infectious viral particles.

Alternatively, the complementary nucleotide sequence(s) may be stably present within a packaging cell line that is included in the kit.

The present invention also relates to a retroviral vector system, which is capable of delivering an RNA genome to a recipient cell, wherein the genome is longer than the wild type genome of the lentivirus. The vector system may, for example, be an EIAV vector system.

Preferably the RNA genome of the vector system has up to 5%, more preferably up to 10% or even up to 30% more bases than the wild-type genome. Preferably the RNA genome is about 10% longer than the wild-type genome. For example, wild type EIAV may comprise an RNA genome of approximately 8 kb. An EIAV vector system of the present invention may have an RNA genome of up to (preferably about) 8.8 kb.

Preferably the retroviral vector system of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs, producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy may also be used to eliminate downstream transcription from the 3' LTR into genomic DNA. This is of particular concern in human gene therapy where it may be important to prevent the adventitious activation of an endogenous oncogene (Yu et al., (1986) PNAS 83: 3194-98; Naviaux et al., (1996) J. Virol. 70: 5701-5; Iwakuma et al., (1999) Virol. 261: 120-32).

Preferably a recombinase-assisted mechanism is used, which facilitates the production of high titer regulated lentiviral vectors from the producer cells of the present invention.

As used herein, the term "recombinase assisted system" includes, but is not limited to, a system using the Cre recombinase/loxP recognition sites of bacteriophage P1 or the site-specific FLP recombinase of *S. cerevisiae*, which catalyses recombination events between 34 bp FLP recognition targets (FRTs).

The site-specific FLP recombinase of *S. cerevisiae*, which catalyses recombination events between 34 bp FLP recognition targets (FRTs), has been configured into DNA constructs to generate high level producer cell lines using recombinase-assisted recombination events (Karreman et al (1996) NAR 24:1616-1624). A similar system has been developed using the Cre recombinase/loxP recognition sites of bacteriophage P1 (Vanin et al (1997) J. Virol 71:7820-7826). This was configured into a lentiviral genome such that high titer lentiviral producer cell lines were generated.

By using producer/packaging cell lines, it is possible to propagate and isolate quantities of retroviral vector particles (e.g. to prepare suitable titers of the retroviral vector particles) for subsequent transduction of, for example, a site of interest (such as adult brain tissue). Producer cell lines are usually better for large-scale production or vector particles.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection may be used to produce the vector before the cells die. Also, cell lines have been developed using transient infection that produce vector titer levels that are better than the levels obtained from stable vector-producing cell lines (Pear et al 1993, PNAS 90:8392-8396).

Producer cells/packaging cells may be of any suitable cell type. Producer cells are generally mammalian cells, but may be, for example, insect cells.

As used herein, the term "producer cell" or "vector producing cell" refers to a cell that contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line that has been screened and selected for high expression of a marker gene. Such cell lines support high-level expression from the retroviral genome. The term "derived producer cell line" is used interchangeably with the term "derived stable producer cell line" and the term "stable producer cell line.

Preferably the derived producer cell line includes, but is not limited to, a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell that contains those elements necessary for production of infectious recombinant virus that are lacking in the RNA genome. Typically, such packaging cells contain one or more producer plasmids, which are capable of expressing viral structural proteins (such as codon optimised gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266), and utilised to create producer cell lines for the production of retroviral vector particles. As already mentioned, a summary of the available packaging lines is presented in "Retroviruses" (as above).

Also as discussed above, simple packaging cell lines, which may comprise a provirus in which the packaging signal has been deleted, have been found to lead to the rapid production of undesirable replication competent viruses through recombination. In order to improve safety, second-generation cell lines have been produced, wherein the 3' LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second-generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example, between the regions of overlap in the gag-pol and env open reading frames.

The packaging cell lines are useful for providing the gene products necessary to encapsidate and provide a membrane protein for a high titer vector particle production. The packaging cell may be a cell cultured in vitro, such as a tissue culture cell line. Suitable cell lines include, but are not limited to, mammalian cells, such as murine fibroblast derived cell lines or human cell lines. Preferably the packaging cell line is a primate or human cell line, such as for example: HEK293, 293-T, TE671, HT1080.

It is highly desirable to use high-titer virus preparations in both experimental and practical applications. Techniques for increasing viral titer include using a psi plus packaging signal as discussed above and concentration of viral stocks.

As used herein, the term "high titer" means an effective amount of a retroviral vector or particle that is capable of transducing a target site such as a cell.

As used herein, the term "effective amount" means an amount of a retroviral or lentiviral vector or vector particle that is sufficient to induce expression of the NOIs at a target site.

A high-titer viral preparation for a producer/packaging cell is usually on the order of $10^5$ to $10^7$ retrovirus particles per mL. For transduction in tissues such as the brain, it is necessary to use very small volumes, so the viral preparation is concentrated by ultracentrifugation. The resulting preparation should have at least $10^8$ t.u./mL, preferably from $10^8$ to $10^9$ t.u./mL, more preferably at least $10^9$ t.u./mL. (The titer is expressed in transducing units per mL (t.u./mL) as titered on a standard D17 cell line). Other methods of concentration such as ultrafiltration or binding to and elution from a matrix may be used.

The expression products encoded by the NOIs may be proteins that are secreted from the cell. Alternatively, the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighboring or distant (e.g. metastatic), which possess a common phenotype.

The presence of a sequence termed the central polypurine tract (cPPT) may improve the efficiency of gene delivery to non-dividing cells. [Charneau and Clavel (1991) J Virol 65:2415-2421; Barry et al (2001) Human Gene Therapy 12:1103-1108] This cis-acting element is located, for example, in the EIAV polymerase coding region element. Preferably the genome of the present invention may comprise a cPPT sequence.

In addition, the viral genome may comprise a translational enhancer.

The NOIs may be operatively linked to one or more promoter/enhancer elements. Transcription of one or more NOIs may be under the control of viral LTRs or alternatively promoter-enhancer elements. Preferably the promoter is a strong viral promoter such as CMV, or is a cellular constitutive promoter such as PGK, beta-actin or EFlalpha. The promoter may be regulated or tissue-specific. The control of expression may also be achieved by using such systems as the tetracycline system that switches gene expression on or off in response to outside agents (in this case tetracycline or its analogues).

In the design of retroviral vector systems, it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example, an env gene from another virus. Pseudotyping is not a new phenomenon and examples may be found in WO 99/61639, WO 98/05759, WO 98/05754, WO 97/17457, WO 96/09400, WO 91/00047 and Mebatsion et al (1997) Cell 90, 841-847.

In a preferred embodiment of the present invention, the vector system is pseudotyped with a gene encoding at least part of the rabies G protein. Examples of rabies G pseudotyped retroviral vectors may be found in WO 99/61639. In a further preferred embodiment of the present invention, the vector system is pseudotyped with a gene encoding at least part of the VSV-G protein. Examples of VSV-G pseudotyped retroviral vectors may be found in U.S. Pat. No. 5,817,491.

It has been demonstrated that a retrovirus or lentivirus minimal system may be constructed from HIV, SIV, FIV, and EIAV viruses. Such a system requires none of the additional genes vif, vpr, vpx, vpu, tat, rev and nef for either vector production or for transduction of dividing and non-dividing cells. It has also been demonstrated that an EIAV minimal vector system may be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous RNA. Thirdly, genes whose function is unknown, such as S2, may be omitted, thus reducing the risk of causing undesired effects. Examples of minimal lentiviral vectors are disclosed in WO 99/32646 and in WO 98/17815.

The absence of functional auxiliary genes from the retroviral vector production system means that those functional genes will also be absent from retroviral vector particles produced by the system. Also, any auxiliary proteins that would otherwise be encoded by those genes and incorporated into the vector particles will be absent from the vector particles. In known retroviral vector production systems, the auxiliary genes may be present as part of the vector genome-encoding DNA, or together with the packaging components. The location of an auxiliary gene in a vector production system depends in part on its relationship with other retroviral components. For example, vif is often part of a gag-pol packaging cassette in a packaging cell. Thus, to remove a functional auxiliary gene for the purposes of the invention may involve its removal from the packaging components, or from the vector genome, or perhaps both.

To remove a functional auxiliary gene may not require removal of the gene in its entirety. Usually removal of part of the gene, or disruption of the gene in some other way will be sufficient. The absence of a functional auxiliary gene is understood herein to mean that the gene is not present in a form in which it is capable of encoding the functional auxiliary protein.

In a preferred system according to the invention, functional vpr and tat genes or analogous genes normally present in the lentivirus on which the vector particles are based are both absent. These two auxiliary genes are associated with characteristics of lentiviruses that are particularly undesirable for a gene therapy vector. However, other than by the proviso given above, the invention is not limited with regard to the combination of auxiliary genes that are absent in a system according to the invention for producing HIV-1-based vector particles, any combination of three, or more preferably four, of the genes may be absent in their functional form. Most preferably, all five of the auxiliary genes vpr, vif, tat, nef, and vpu are absent in their functional form. Similarly, for systems concerned with other lentiviruses, it is most preferable that all of the auxiliary genes are absent in their functional form (except rev which is preferably present unless replaced by a system analogous to the rev/RRE system).

Thus, preferably, the delivery system used in the invention is devoid of at least tat and S2 (if it is an EIAV vector system), and possibly also vif, vpr, vpx, vpu and nef. More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE may be reduced or eliminated by codon optimisation (see below) or by replacement with other functional equivalent systems such as the MPMV system. As expression of the codon-optimised gag-pol is rev-independent, RRE may be removed from the gag-pol expression cassette, thus removing any potential for recombination with any RRE contained on the vector genome.

In a preferred embodiment, the viral genome of the present invention lacks the Rev response element (RRE). In another preferred embodiment, a nucleic acid sequence encoding Rev, or a functional equivalent thereof, is disrupted such that the nucleic acid sequence is incapable of encoding the functional Rev or is removed from the vector genome.

In a preferred embodiment, the system used in the present invention is based on a so-called "minimal" system in which some or all of the additional genes have been removed. Preferably the viral vector of the present invention has a minimal viral genome.

As used herein, the term "minimal viral genome" means that the viral vector has been manipulated so as to remove the non-essential elements and to retain the essential elements to provide the required functionality to infect, transduce and deliver a NOI to a target host cell.

Preferably the viral vector with the minimal viral genome is a minimal lentiviral vector.

Codon optimization has previously been described in WO99/41397. Different cells differ in their usage of particular codons. This codon bias corresponds to a bias in the relative abundance of particular tRNAs in the cell type. By altering the codons in the sequence to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells may be achieved. Codon usage tables are known in the art for mammalian cells, as well as for a variety of other organisms.

Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev independent. Codon optimization also reduces homologous recombination between different constructs within the vector system (for example, between the regions of overlap in the gag-pol and env open reading frames). The overall effect of codon optimization is therefore a notable increase in viral titer and improved safety.

In one embodiment, only codons relating to INS are codon optimized. However, in a much more preferred and practical embodiment, the sequences are codon optimized in their entirety, with the exception of the sequence encompassing the frameshift site.

The gag-pol gene has two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV, the beginning of the overlap has been taken to be nt 1262 (where nucleotide 1 is the A of the gag ATG). The end of the overlap is at 1461 bp. To ensure that the frameshift site and the gag-pol overlap are preserved, the wild type sequence has been retained from nt 1156 to 1465.

Derivations from optimal codon usage may be made, for example, to accommodate convenient restriction sites, and conservative amino acid changes may be introduced into the gag-pol proteins.

In a highly preferred embodiment, codon optimization was based on highly expressed mammalian genes. The third and sometimes the second and third base may be changed.

Due to the degenerate nature of the Genetic Code, it will be appreciated that a skilled worker may achieve numerous gag-pol sequences. Also, there are many retroviral variants described that may be used as a starting point for generating a codon optimized gag-pol sequence. Lentiviral genomes may be quite variable. For example, there are many quasi-species of HIV-1 that are still functional. This is also the case for EIAV. These variants may be used to enhance particular parts of the transduction process. Details of HIV variants may also be found in the HIV databases maintained by Los Alamos National Laboratory. Details of EIAV clones may be found at the NCBI database maintained by the National Institutes of Health.

The strategy for codon optimized gag-pol sequences may be used in relation to any retrovirus. This would apply to all lentiviruses, including EIAV, FIV, BIV, CAEV, VMR, SIV, HIV-1 and HIV-2. In addition, this method could be used to increase expression of genes from HTLV-1, HTLV-2, HFV, HSRV and human endogenous retroviruses (HERV), MLV and other retroviruses.

Codon optimization may render gag-pol expression Rev independent. To enable the use of anti-rev or RRE factors in the retroviral vector, however, it would be necessary to render the viral vector generation system totally Rev/RRE independent. Thus, the genome also needs to be modified.

This is achieved by optimizing vector genome components. Advantageously, these modifications may also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titer. To date, efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-terminal 360 nucleotides or so in gag leads to an increase in vector titer. Thus, preferably, the retroviral vector genome includes a gag sequence that may comprise one or more deletions, more preferably the gag sequence which may comprise about 360 nucleotides derivable from the N-terminus.

In the present invention, the term NOI (nucleotide sequence of interest) includes any suitable nucleotide sequence, which is not necessarily a complete naturally occurring DNA or RNA sequence. Thus, the NOI may be, for example, a synthetic RNA/DNA sequence, a codon optimized RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence may be in a sense orientation or in an anti-sense orientation. Preferably, it is in a sense orientation. Preferably, the sequence is, may comprise, or is transcribed from cDNA.

The NOI(s), also referred to as "heterologous sequence(s)", "heterologous gene(s)" or "transgene(s)", may be any one or more of, for example, a selection gene(s), marker gene(s) and therapeutic gene(s).

The NOI may be a candidate gene that is of potential significance in a disease process. Thus the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, small interfering RNA (siRNA), a transdominant negative mutant of a target protein, a toxin, a conditional toxin, an antigen, a tumor suppresser protein and growth factors, membrane proteins, pro- and anti-angiogenic proteins and peptides, vasoactive proteins and peptides, anti-viral proteins and ribozymes, and derivatives thereof (such as with an associated reporter group). The NOIs may also encode pro-drug activating enzymes. When used in a research context, the NOIs may also encode reporter genes such as, but not limited to, green fluorescent protein (GFP), luciferase, beta-galactosidase, or resistance genes to antibiotics such as, for example, ampicillin, neomycin, bleomycin, zeocin, chloramphenicol, hygromycin, kanamycin, among others.

The NOI may encode all or part of the protein of interest ("POI"), or a mutant, homologue or variant thereof. For example, the NOI may encode a fragment of the POI that is capable of functioning in vivo in an analogous manner to the wild-type protein.

The term "mutant" includes POIs that include one or more amino acid variations from the wild-type sequence. For example, a mutant may comprise one or more amino acid additions, deletions or substitutions.

Preferably the NOI encodes a single POI or a mutant, homologue or variant thereof. In a highly preferred embodiment, the NOI does not encode a fusion protein. As used herein, the term "fusion protein" is used in its conventional sense to mean an entity that may comprise two or more protein activities, joined together by a peptide bond to form a single chimeric protein. A fusion protein is encoded by a single polynucleotide driven by a single promoter.

The viral genome of the present invention may comprise at least one, but may optionally comprise two or more NOIs. In order for two or more NOIs to be expressed, there may be two or more transcription units within the vector genome, one for each NOI. However, it is clear from the literature that retroviral vectors achieve the highest titers and most potent gene expression properties if they are kept genetically simple [WO96/037623; Bowtell et al., (1988) J. Virol. 62, 2464; Correll et al., (1994) Blood 84, 1812; Emerman and Temin (1984) Cell 39, 459; Ghattas et al., (1991) Mol. Cell. Biol. 11, 5848]. Thus, it is preferable to use an internal ribosome entry site (IRES) to initiate translation of the second (and subsequent) coding sequence(s) in a polycistronic (or as used herein, "multicistronic") message [Adam et al (1991) J. Virol. 65, 4985].

Insertion of IRES elements into retroviral vectors is compatible with the retroviral replication cycle and allows expression of multiple coding regions from a single promoter (Adam et al (as above); Ngoi et al (2004) Curr Gene Ther 4(1):15-31; Chen et al (1993) J. Virol 67:2142-2148). When located between open reading frames in an RNA, IRES elements allow efficient translation of the downstream open reading frame by promoting entry of the ribosome at the IRES element followed by downstream initiation of translation.

As used herein, the term "cistron" refers to a nucleic acid segment corresponding to a polypeptide chain, which may comprise the relevant translational start (initiation) and stop (termination) codons. A multicistronic mRNA is an mRNA transcript with more than one cistron and thus, encoding more than one polypeptide.

According to WO 97/14809, IRES sequences are typically found in the 5' non-coding region of genes. In addition to those in the literature they may be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

For the IRES to be capable of initiating translation of each NOI, it should be located between or prior to NOIs in the vector genome. For example, for a multicistronic sequence containing n NOIs, the genome may be as follows: $[NOI_1\text{-}IRES_1] \ldots [IRES_{(n-1)}\text{-}NOI_n]$.

For bi and tricistronic sequences, the order may be as follows: $NOI_1\text{-}IRES_1\text{-}NOI_2$ $NOI_1\text{-}IRES_1\text{-}NOI_2\text{-}IRES_2\text{-}NOI_3$.

Alternative configurations of IRESs and NOIs may be utilized. For example transcripts containing the IRESs and NOIs need not be driven from the same promoter.

An example of this arrangement may be: $IRES_1\text{-}NOI_1\text{-}$promoter$\text{-}NOI_2\text{—}IRES_2\text{-}NOI_3$.

Preferably, in any construct utilising an internal cassette having more than one IRES and NOI, the IRESs may be of different origins, that is, heterologous to one another. For example, one IRES may be from EMCV and the other IRES may be from poliovirus.

Although IRESs are an efficient way to co-express multiple genes from one vector, other methods are also useful, and may be used alone or in conjunction with IRESs. These include the use of multiple internal promoters in the vector [Overell et al. (1988), Mol Cell Biol. 8: 1803-8], or the use of alternate splicing patterns leading to multiple RNA species derived from the single viral genome that expresses the different genes.

The present invention also relates to a cell that has been transduced with a vector system which may comprise a viral genome according to the first aspect of the invention.

The cell may be transduced in vivo, in vitro or ex vivo. For example, if the cell is a cell from a mammalian subject, the cell may be removed from the subject and transduced ready for reimplantation into the subject (ex vivo transduction). Alternatively, the cell may be transduced by direct gene transfer in vivo, using the vector system of the present invention in accordance with standard techniques (such as via injection of vector stocks expressing the NOIs). If the cell is part of a cell line that is stable in culture (i.e. which may survive numerous passages and may multiple in vitro) then it may be transduced in vitro by standard techniques, for example, by exposure of the cell to viral supernatants which may comprise vectors expressing the NOIs.

The cell may be any cell that is susceptible to transduction. If the vector system is capable of transducing non-dividing cells (for example if it is a lentiviral system) then the cell may be a non-dividing cell, such as a neuron.

The present invention may employ cassettes which may comprise one or more NOIs, which, in the case of two or more NOIs, may be operably linked by an IRES. These cassettes may be used in a method for producing the vector genome in a producer cell.

The present invention also provides an expression vector which may comprise such a cassette. Transfection of a suitable cell with such an expression vector should result in a cell that expresses each POI encoded by the NOI in the cassette. The present invention also provides such a transfected cell.

Cloning of the cassette into an expression vector and transfection of cells with the vector (to give expression of the cassette) may be carried out by techniques well known in the art (such as those described in Sambrook et al. (Molecular Cloning: A Laboratory Manual, 2nd Edition, Cold Spring Harbor Laboratory press (1989)), and other laboratory textbooks).

Preferably the cassette may comprise a promoter. A cassette which may comprise two or more NOIs may be bicistronic or tricistronic, and may comprise the following elements: Promoter-$(NOI_1)$-$(IRES_1)$-$(NOI_2)$ Promoter-$(NOI_1)$-$(IRES_1)$-$(NOI_2)$-$(IRES_2)$-$(NOI_3)$.

The present invention provides a pharmaceutical composition, which may comprise a vector genome according to the second aspect of the invention and a pharmaceutically acceptable carrier, diluent or excipient (including combinations thereof).

The pharmaceutical compositions may be for human or animal usage in human and veterinary medicine or research, and may typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent may be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilizing agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavoring or coloring agents, or they may be injected parenterally, for example, intravenously, intramuscularly or subcutaneously. For parenteral administration, the compositions may be best used in the form of a sterile aqueous solution, which may contain other substances, for example, enough salts or monosaccharides to make the solution isotonic with blood. For buccal or sublingual administration, the compositions may be administered in the form of tablets or lozenges that may be formulated in a conventional manner.

Typically, a physician will determine the actual dosage that will be most suitable for an individual subject and it will vary with the age, weight and response of the particular patient and severity of the condition. The dosages below are exemplary of the average case. There may, of course, be individual instances where higher or lower dosage ranges are merited.

The compositions (or component parts thereof) of the present invention may be administered orally. In addition, or in the alternative, the compositions (or component parts thereof) of the present invention may be administered by direct injection. In addition, or in the alternative, the compositions (or component parts thereof) of the present invention may be administered topically. In addition, or in the alternative, the compositions (or component parts thereof) of the present invention may be administered by inhalation. In addition, or in the alternative, the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" also includes, but is not limited to, delivery by a mucosal route, for example, as a nasal spray or aerosol for inhalation or as an ingestible solution; a parenteral route where delivery is by an injectable form, such as, for example, an intravenous, intramuscular or subcutaneous route.

Hence, one or more of the following routes may administer the pharmaceutical composition of the present invention: oral administration, injection (such as direct injection), topical, inhalation, parenteral administration, mucosal administration, intramuscular administration, intravenous administration, subcutaneous administration, intraocular administration or transdermal administration.

Pharmaceutical compositions which may comprise an effective amount of vector which may comprise an identified modulating moiety operably linked to an NOI may be used in the treatment of disorders, such as those listed in WO 98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated Fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillain-Barre syndrome, Sydenham chora, myasthenia gravis, pseudo-tumor cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumors; blood born tumors such as leukemias; tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronary collaterals; cerebral collaterals; arteriovenous malformations; ischaemic limb angiogenesis; neovascular glaucoma; retrolental fibroplasia; diabetic neovascularization; *Helicobacter*-related diseases, fractures, vasculogenesis, hematopoiesis, ovulation, menstruation and placentation.

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

EXAMPLES

Example 1

Removal of the Woodchuck Hepatitis Virus Post-Transcriptional Regulatory Element (WPRE) to Increase the Safety Profile of Viral Vectors A study was conducted to evaluate the effects of removal of the WPRE on the levels of protein expression from retroviral vectors.

Methods

Construction of the Transfer Plasmids 'pELNS Luc ADB678' 'pELNS LucNoX ADB679' and 'pELNS LucNoW ADB680'

Figure 2:
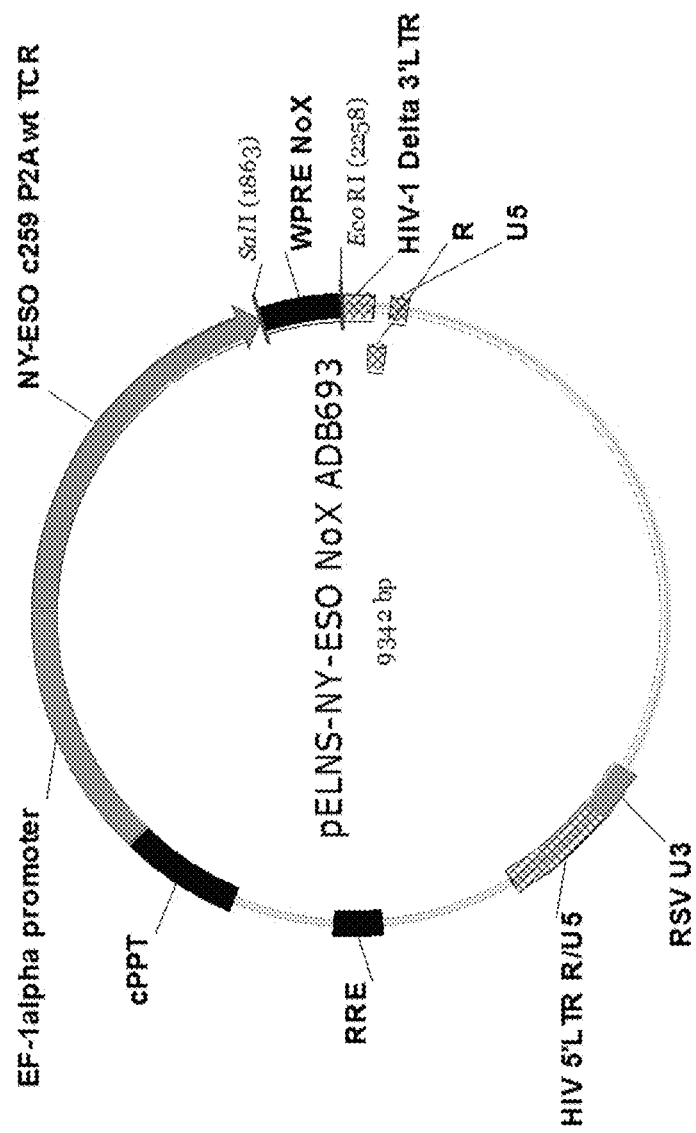
FIG. 2 is a schematic map of plasmid designated pELNS-NY-ESO NoX ADB693. A modification has been made to the WPRE region of the pELNS-NY-ESO ADB152 plasmid to remove the X-promoter and truncated X-protein at the 3'-end.

Based on the pELNS-NY-ESO ADB152 plasmid (FIG. 1) two variants designated pELNS-NY-ESO NoX ADB693 and pELNS-NY-ESO NoW ADB694 have been constructed. For the construction of pELNS-NY-ESO NoX ADB693, the WPRE region of the pELNS-NY-ESO ADB152 plasmid was modified by PCR amplification using forward primer [nucleotide sequence: cgGTCGACaatcaacctctggattac] and reverse primer [nucleotide sequence: cgGAATTCgacaacac-cacggaattgtc] using Platinum Taq DNA polymerase PCR kit (Life Technologies Catalog #11304011). The PCR product was digested with SalI and EcoRI restriction enzymes followed by purification using Zymo Clean & Concentrator kit (Zymo Research cat. No. D4005). The purified fragment was then ligated into SalI_EcoRI digested pELNS-NY-ESO ADB152 plasmid backbone fragment to form the pELNS-NY-ESO NoX ADB693 plasmid (FIG. 2).

For the generation of pELNS-NY-ESO NoW ADB694 plasmid, two 5'-phosphorylated oligonucleotides [top strand oligonucleotide sequence: tcgacTCTAGAg; bottom strand oligonucleotide sequence: aattcTCTAGAg] were annealed to form a linker containing SalI_XbaI_EcoRI sites with 'sticky' SalI and EcoRI restriction enzyme ends:

Figure 3:
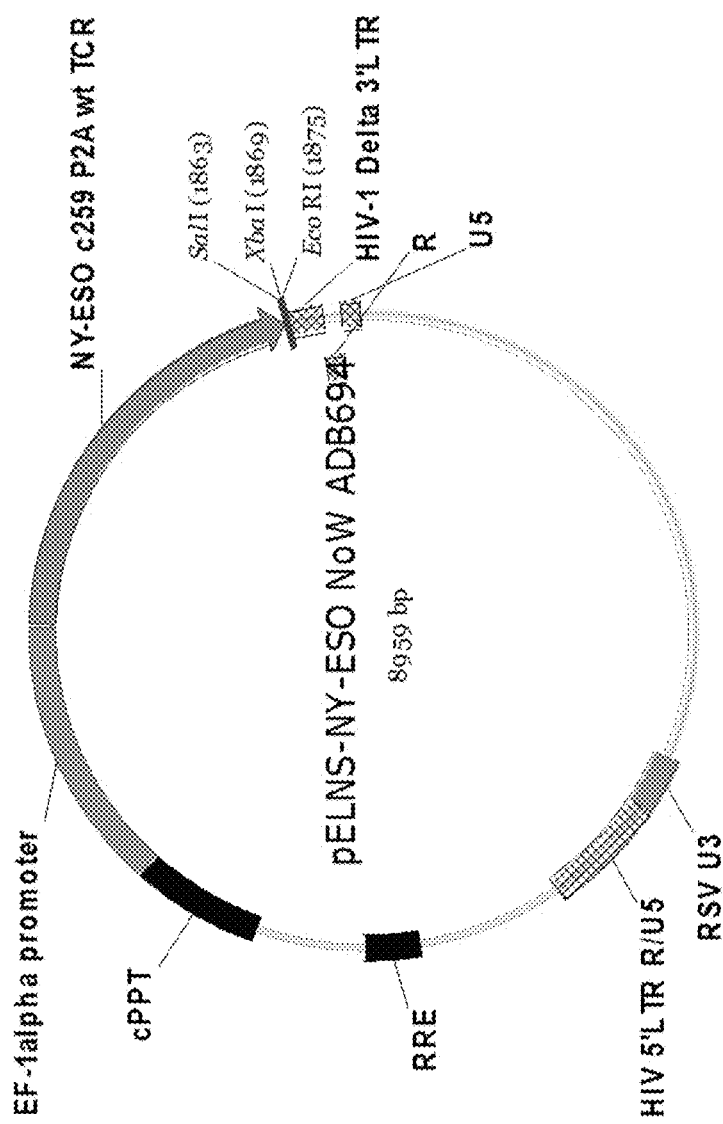
FIG. 3 is a schematic map of plasmid designated pELNS-NY-ESO NoW ADB694. A modification has been made to the WPRE region of the pELNS-NY-ESO ADB152 plasmid to replace the WPRE region with 6 nucleotides (TCTAGA) i.e. an XbaI restriction enzyme site.

The annealed linker was then ligated into SalI_EcoRI digested pELNS-NY-ESO ADB152 plasmid backbone fragment to form the pELNS-NY-ESO NoW ADB694 plasmid (FIG. 3).

Then the pELNS-NY-ESO ADB152, pELNS-NY-ESO NoX ADB693 and pELNS-NY-ESO NoW ADB694 plasmids were used to generate pELNS Luc ADB678, pELNS LucNoX ADB679 and pELNS LucNoW ADB680 plasmids respectively.

Figure 4:
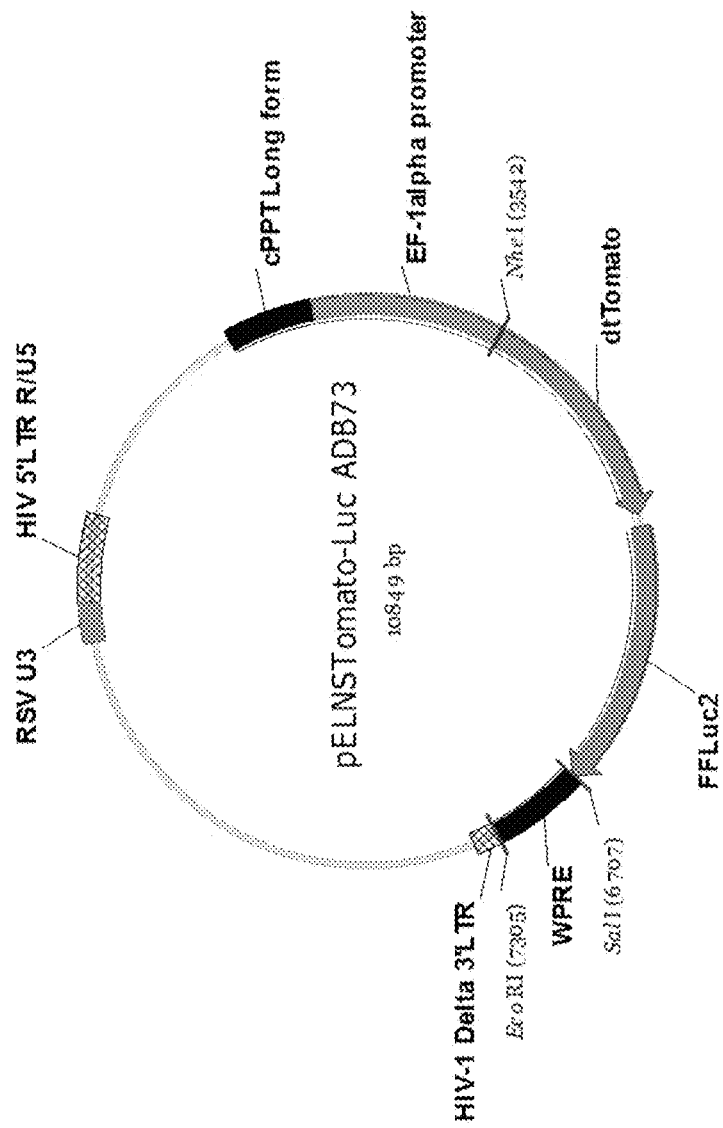
FIG. 4 is a schematic map of plasmid designated pELNS Tomato-Luc ADB73
Figure 5:
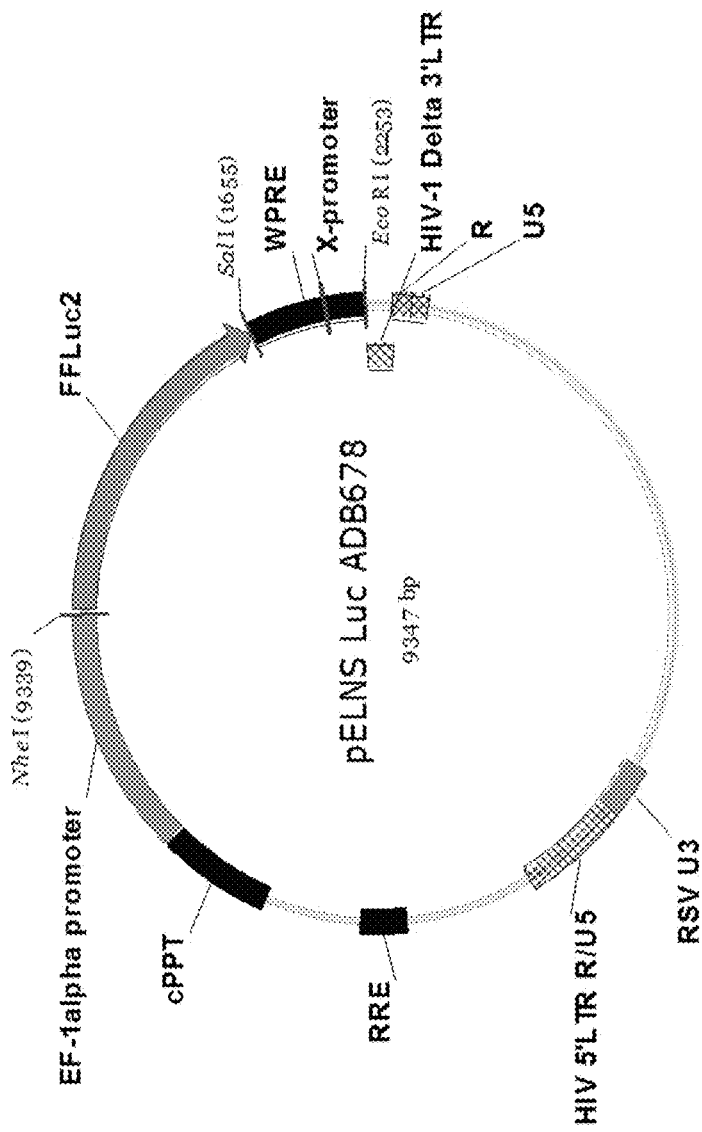
FIG. 5 is a schematic map of plasmid designated pELNS Luc ADB678.
Figure 6:
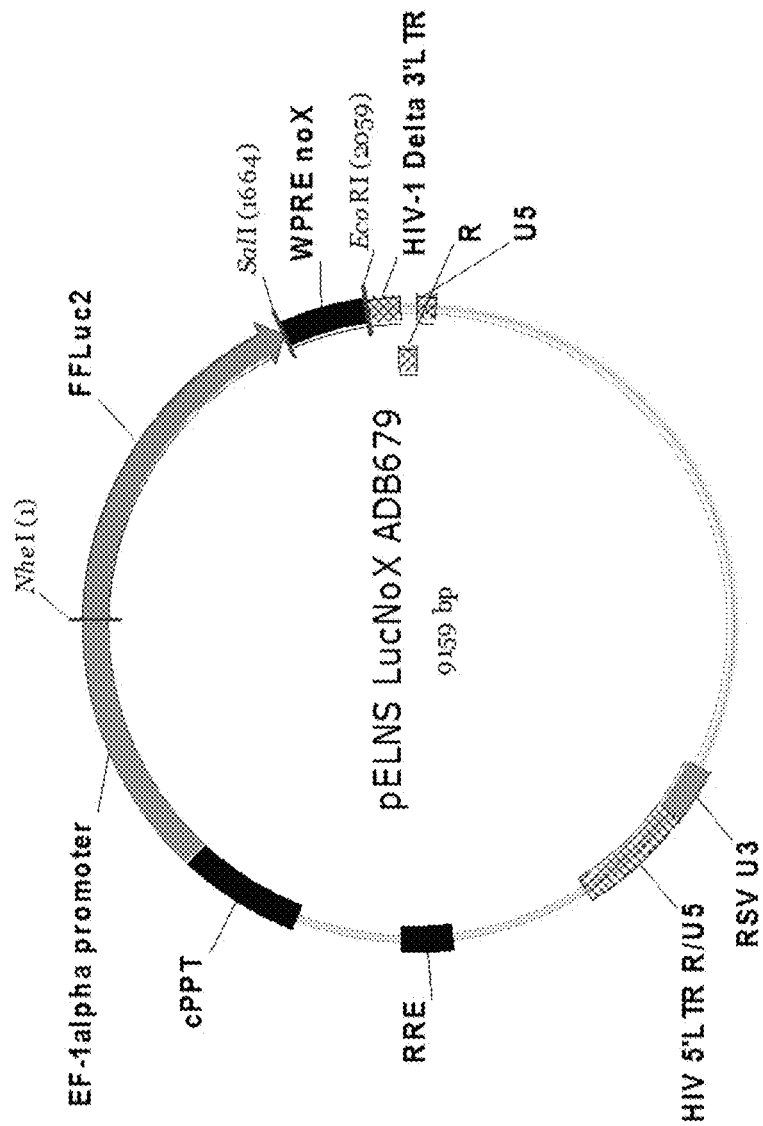
FIG. 6 is a schematic map of plasmid designated pELNS LucNoX ADB679.
Figure 7:
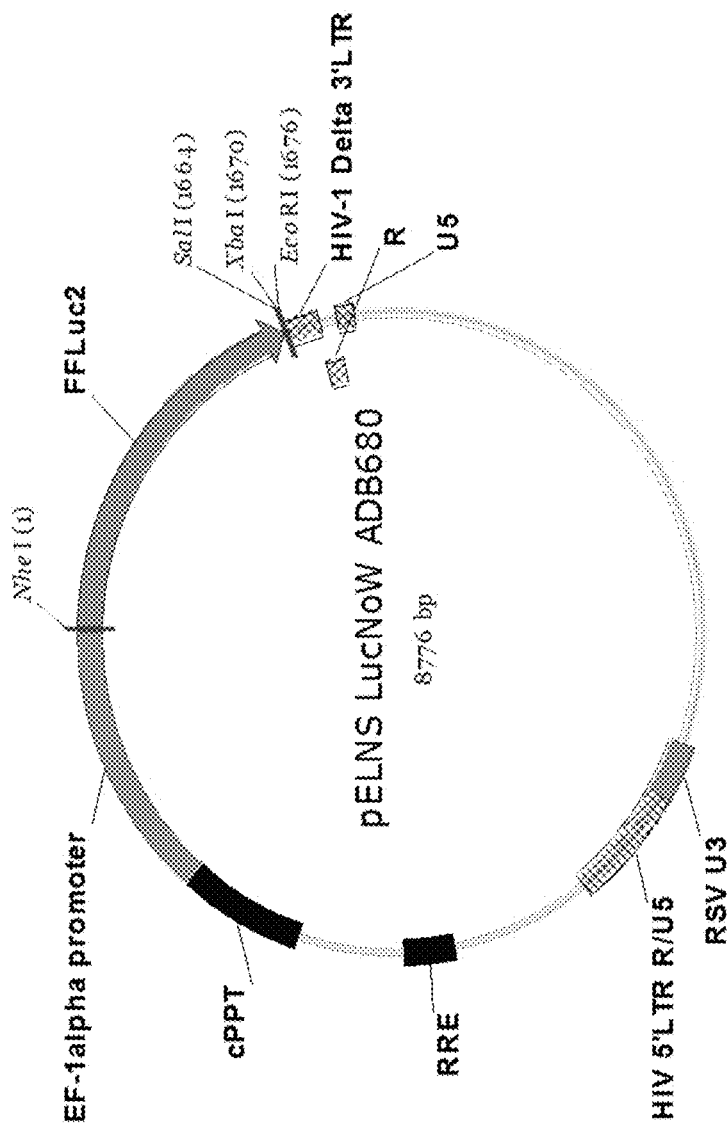
FIG. 7 is a schematic map of plasmid designated pELNS LucNoW ADB680.

For the generation of the pELNS Luc ADB678 plasmid, a luciferase reporter gene [flanked by an NheI restriction enzyme site at the 5'-end and a SalI site at the 3'-end] was amplified from the pELNS Tomato-Luc ADB73 plasmid (FIG. 4) by PCR using forward primer [nucleotide sequence: ACTGGCTAGCCACCatggaagatgccaaaaaca] and reverse primer [nucleotide sequence: gaggttgattgtcgacttac]. The PCR product was digested with NheI and SalI restriction enzymes followed by purification using Zymo Clean & Concentrator kit. The purified fragment was then ligated into NheI_SalI digested pELNS-NY-ESO ADB152, pELNS-NY-ESO NoX ADB693 and pELNS-NY-ESO NoW ADB694 plasmid backbone fragments to generate pELNS Luc ADB678, pELNS LucNoX ADB679 and pELNS LucNoW ADB680 plasmids respectively (FIGS. 5-7).

Production of Recombinant Lentiviral Vector Expressing Luciferase

Recombinant lentiviral vector was produced using the human HEK293T cell line as the host by transient transfection of 4 plasmids—a transfer plasmid containing the luciferase reporter gene expression cassette and three packaging plasmids expressing the structural HIV-1 gag-pol gene, accessory gene rev or viral envelope Vesicular stomatitis virus glycoprotein (VSV-G). Supernatant was collected 48 hours post-transfection and cell debris was removed by filtration through a 0.45 μm filter. The lentiviral vector particles were then concentrated from the clarified supernatant by ultra-centrifugation at 10,000×g for 16-18 hours. The pellet of viral particles was finally resuspended in an appropriate volume of culture medium.

Lentiviral vector produced with pELNS Luc ADB678 [full length WPRE element], pELNS LucNoX ADB679 [WPRE element truncated by removal of the X-promoter and the truncated X-protein at the 3'-end] or pELNS LucNoW ADB680 [WPRE element replaced by 6 nucleotides. TCTAGA]transfer plasmid was designated as 'Luc', 'LucNoX' or 'LucNoW' vectors respectively.

Measurement of the Level of Intact Vector Particles in Lentiviral Vector Preparation The level of intact lentiviral vector particles were determined using the QuickTiter Lentivirus Titer Kit (Cell Biolabs Inc, cat. No. VPK-107). This assay kit measures only lentiviral vector particle associated p24 gag capsid proteins but not the free p24 proteins present in the viral vector preparation. Therefore the results of this assay may be used as a surrogate for the biological titer of the lentiviral vector.

Lentiviral Vector Transduction of Target Cells—SupT1 Cell Line and Primary T Cells from Donors and Cell Pellet Harvest The expression of luciferase reporter gene in target cells was evaluated by transducing either human SupT1 cell line or primary T cells from various donors. For the transduction of SupT1 cells, SupT1 cells were pelleted and resuspended in fresh culture medium. These cells were seeded at a density of $1 \times 10^6$ cell/well at 0.5 mL per well in a 24-well plate. Then 0.5 mL of lentiviral vector [Luc, LucNoX or LucNoW] was added to the well. Transduced SupT1 cells were harvested as cell pellets [300×g for 5 minutes] for the measurement of luciferase expression 48 hours later.

For the transduction of primary T cells from donors, leukocytes including T cells were isolated from donor's whole blood using Lymphoprep kit (Axis-Shield, cat#NYC-1114547) according to manufacturer's instructions. CD14 and CD25 positive leukocytes were removed from this population by incubating with appropriate amount of human CD14 and CD25 microbeads (Miltenyi Biotech cat #130-050-201, 130-092-983) followed by separation with Miltenyi LS columns (Miltenyi Biotec cat #130-042-401). Appropriate amounts of the remaining cells were incubated with appropriate amount of recombinant interleukin-2 and appropriate amount of anti-CD3/anti-CD28 beads. After an overnight incubation, these cells were transferred to a 24-well plate at $10^6$ cells/well in 1 mL volume. Then 1 mL of lentiviral vector [Luc, LucNoX or LucNoW] was added to the well. Transduced primary T cells were harvested as cell pellets [300×g for 5 minutes] for the measurement of luciferase expression 48 hours later.

Expression of Active Luciferase in SupT1 Cells Transduced with Serial Dilutions of Luc, LucNoX and LucNoW Vectors Expressing the Luciferase Reporter Gene SupT1 cell pellets were incubated with appropriate amount of cold Glo Lysis Buffer (Promega E2661) on ice for >5 minutes after vigorous vortexing for 1 min. The cell lysates were then kept on ice until use. A luciferase standard curve was generated using appropriate amount of Quanti-Lum recombinant Luciferase (Promega E1701) diluted in Glo Lysis buffer. Then the appropriate amounts of standards and samples were added to the wells of a solid-wall white 96-well plate (Greiner Bio Cat #655083). To each well 100 μL of reconstituted Bright-Glo™ Luciferase Assay Substrate (Promega E2620) equilibrated to room temperature were added. The luminescence (relative light unit, RLU) of each well corresponding to the level of luciferase expression was measured by a Wallac Victor2 1420 plate reader (Perkin Elmer). The luminescence of each sample well was converted to the concentration of active luciferase in ng/mL using a standard curve.

Results

Figure 8:
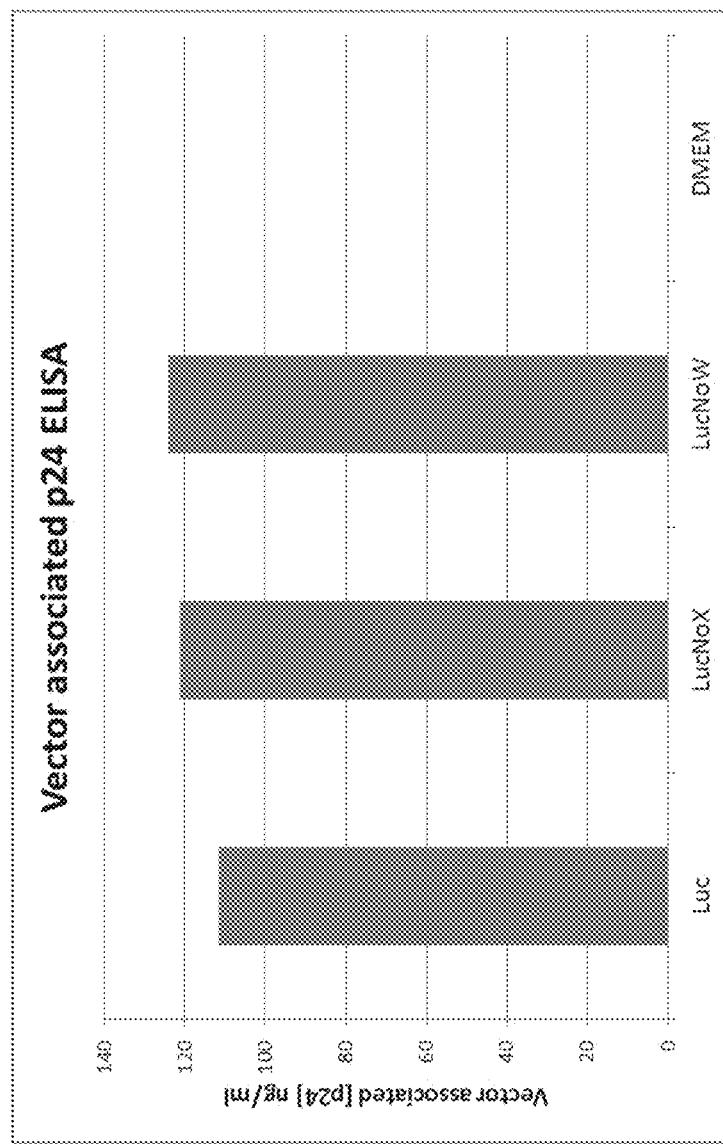
FIG. 8 is a graph showing the levels of lentiviral vector associated p24 gag capsid proteins present in Luc, LucNoX and LucNoW lentiviral vector preparations.

Measurement of the Level of Intact Vector Particles in Lentiviral Vector Preparation As shown in FIG. 8, the levels of lentiviral vector associated p24 gag capsid proteins were similar in Luc, LucNoX and LucNoW lentiviral vector preparations. This suggests that these lentiviral vector preparations contained similar level of vector particles. The full culture medium [Dulbecco's Modified Eagle Medium (DMEM) culture medium supplemented with 10% v/v fetal bovine serum (FBS) and 2 mM GlutaMaX] which was used to resuspend the viral vector pellets of these vectors did not contribute to any background signal.

Figure 9:
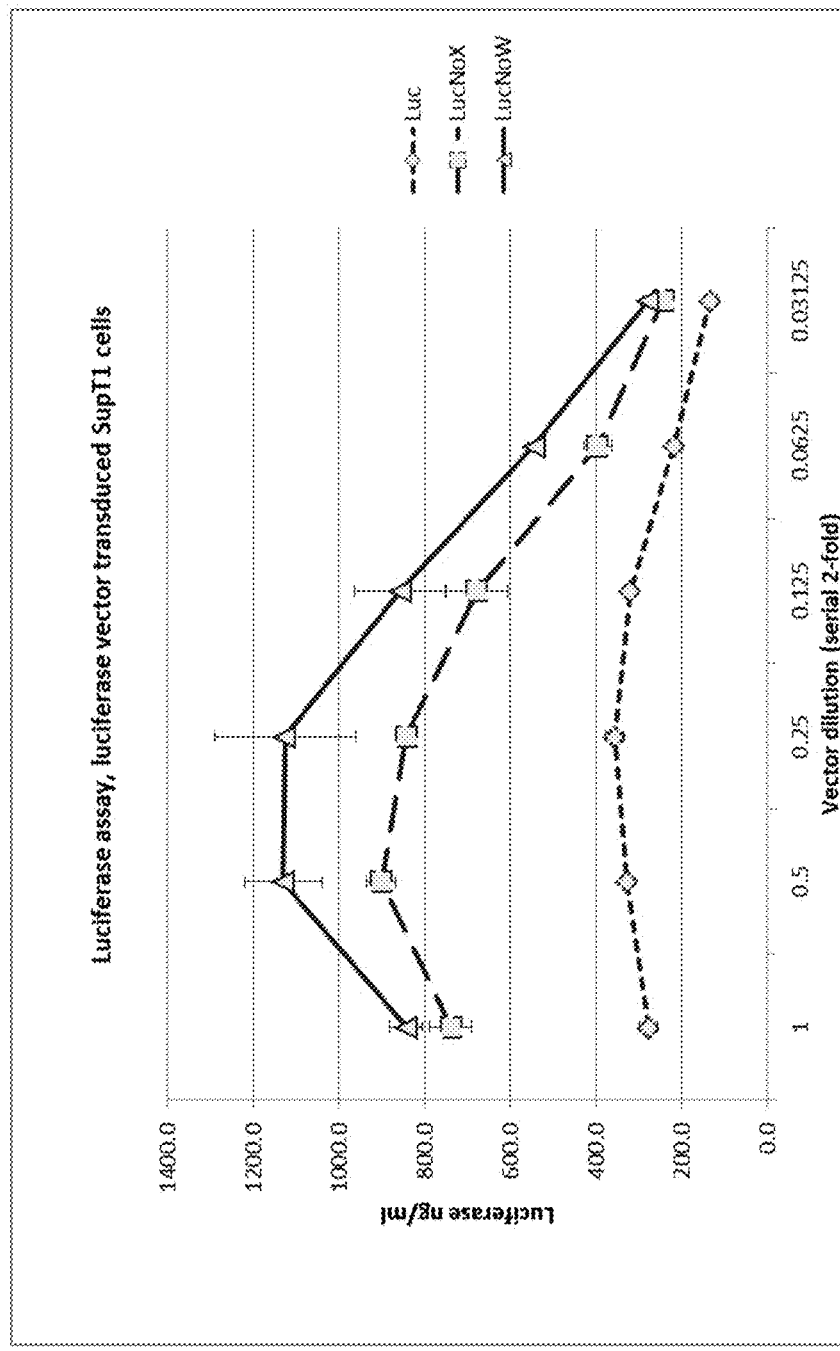
FIG. 9 is a graph showing the expression of luciferase activities in SupT1 cells transduced with serial dilutions of Luc, LucNoX and LucNoW vectors.

Lentiviral Vector Transduction of Target Cells—SupT1 Cell Line and Primary T Cells from Donors and Cell Pellet Harvest The results shown in FIG. 9 show that SupT1 cells transduced with the LucNoX lentiviral vector produced with transfer plasmids pELNS LucNoX ADB679 expressed slightly better luciferase activities than those with the Luc control vector produced with pELNS Luc ADB678 plasmid over a range of vector dilutions. This is expected as lentiviral vector produced with a transfer plasmid containing a WPRE mutant which does not express X protein has previously been shown to be functionally similar to the full length WPRE with respect to enhancement of transgene expression [Gonzalez-Murillo A. et al (2010). Hum Gene Ther 21(5): 623-30; Schambach A. et al (2006) Gene Ther 13(7):641-5].

Moreover, cells transduced with the LucNoW lentiviral vector produced with transfer plasmid pELNS LucNoW ADB680 expressed slightly better luciferase activities than those with the Luc control too, over a range of vector dilutions (FIG. 9). This shows that six nucleotides, TCTAGA (an XbaI restriction enzyme site) may be used in place of a functional WPRE element.

Expression of Active Luciferase in SupT1 Cells or Primary T Cells Transduced with Luc, LucNoX and LucNoW Vectors Expressing the Luciferase Reporter Gene To further evaluate whether the results could be reproduced in primary T cells, the above experiment was repeated using the highest doses of the same batches of Luc, LucNoX and LucNoW vectors. Also, the same batch of SupT1 cells was used as the control.

Figure 10:
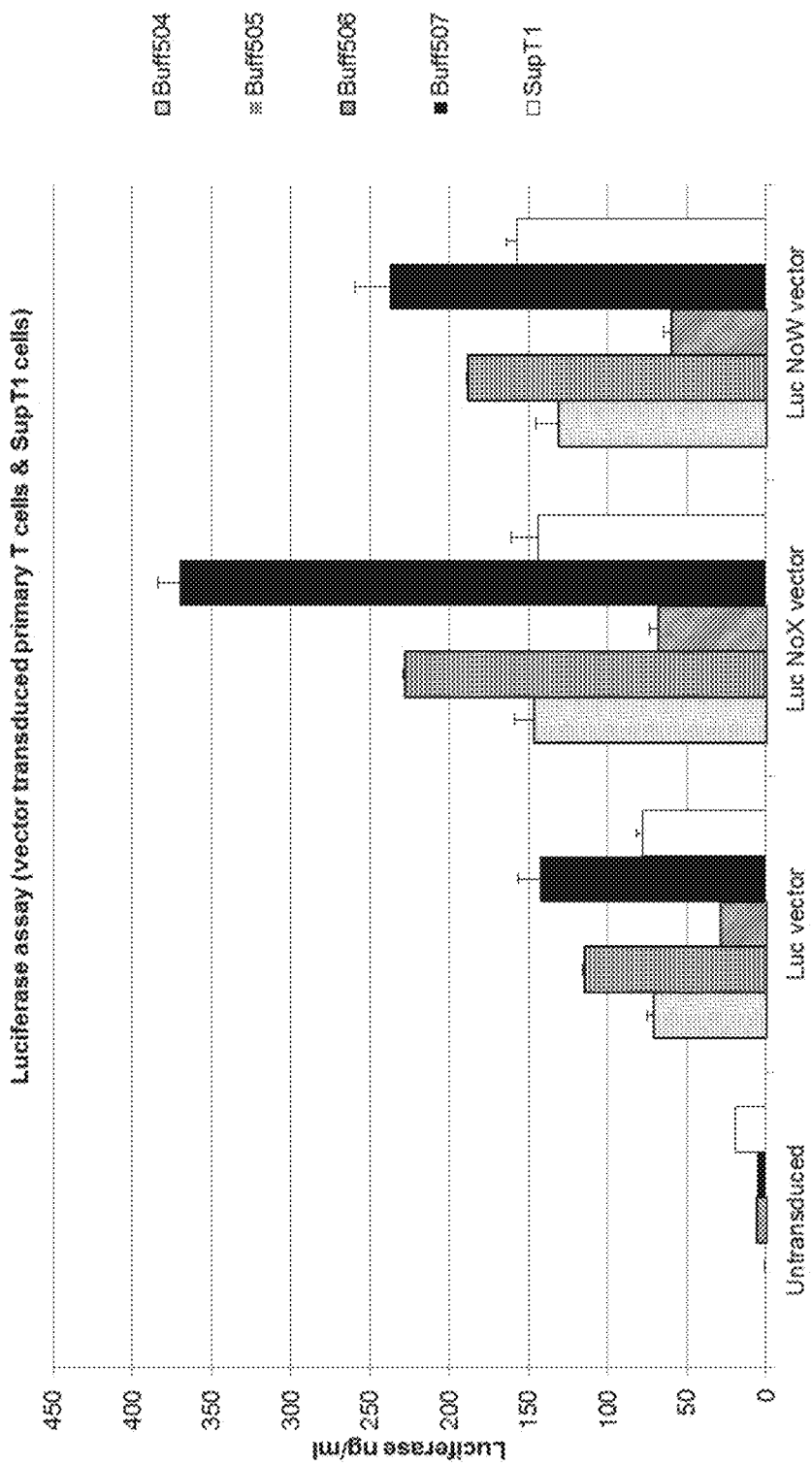
FIG. 10 is a graph showing the expression of luciferase activities in SupT1 and primary T cells from four different donors designated Buff504, Buff505, Buff506 and Buff507.

As shown in FIG. 10, primary T cells isolated from four different donors as well as SupT1 transduced with the LucNoX lentiviral vector expressed higher luciferase activities than those with the Luc control vector.

Additionally, cells transduced with the LucNoW lentiviral vector expressed higher luciferase activities than those with the Luc control or the LucNoX vectors (FIG. 10). This is in agreement with the results of the previous experiment that the whole WPRE element could be replaced by a short spacer element, without any impact on the vector titer.

Example 2

Construction of the Plasmids NoWPRE 0 mer, NoWPRE 3 mer No WPRE 10 mer, NoWPRE 20 mer, No WPRE 30 mer No WPRE 40 mer and No WPRE 50 mer The "Luc NoW 0 mer" plasmid was generated by digesting ADB680 plasmid (FIG. 7) with SalI and EcoRI. Then the vector backbone fragment was filled in with T4 polymerase followed by ligation. The new plasmid no longer contained SalI and EcoRI sites (FIG. 2).

The generation of the plasmids was by annealing two complementary oligos to form the (randomly selected) stuffer sequence with ready-to-ligate SalI & EcoRI restriction site compatible ends (see table 1). The annealed stuffer sequences were then ligated into SalI & EcoRI digested ADB 680 plasmid backbone to form the corresponding plasmids. These plasmids contained a SalI and an EcoRI restriction site.

TABLE 1

Annealed linker containing stuffer sequence with ready-to-ligate SalI and EcoRI restriction sites compatible ends (in bold):

| Stuffer sequence length | Linker sequences |
|---|---|
| 3 mer | SalI              EcoRI<br>TCGACT CTG<br>         GA GACTTAA |
| 10 mer | SalI                     EcoRI<br>TCGACG CAACTAGAAG<br>         GC GTTGATCTTC TTAA |
| 20 mer | SalI                                      EcoRI<br>TCGACA CCAAGCTGGA CATCTACCCG<br>         GT GGTTCGACCT GTAGATGGGC TTAA |
| 30 mer | SalI<br>TCGACC CGAAGGAGTA CTATAAACCG<br>         GG GCTTCCTCAT GATATTTGGC<br><br>                                  EcoRI<br>CCATACGGAG<br>GGTATGCCTC TTAA |
| 40 mer | SalI<br>TCGACG GCGAGTTAA AACCTCTTGC<br>         GC CGCTCAAATT TTGGAGAACG<br><br>                                  EcoRI<br>TACATCGCCT CATCTGTGAG<br>ATGTAGCGGA GTAGACACTC TTAA |
| 50 mer | SalI<br>TCGACG TGACGAACAT GGGGCAGATT<br>         GC ACTGCTTGTA CCCCGTCAA<br><br>                                  EcoRI<br>GCTTCCAGTG CTTGCTGGGC ATTGCTGATG<br>CGAAGGTCAC GAACGACCCG TAACGACTAC TTAA |

The inserted stuffer sequences are therefore as follows:

TCT
SEQ ID NO: 2

GCAACTAGAA
SEQ ID NO: 3

ACCAAGCTGGACATCTACCC
SEQ ID NO: 4

CCGAAGGAGTACTATAAACCGCCATACGGA
SEQ ID NO: 5

GGCGAGTTTAAAACCTCTTGCTACATCGCCTCATCTGTGA
SEQ ID NO: 6

GTGACGAACATGGGGCAGATTGCTTCCAGTGCTTGCTGGGCATTGCTGAT
SEQ ID NO: 7

Production of Recombinant Lentiviral Vector Expressing Either Luciferase or NYESO-1 TCR Recombinant lentiviral vector was produced using the human HEK293T cell line as the host by transient transfection of 4 plasmids—a transfer plasmid contains a luciferase reporter or NYESO-1 T cell receptor (TCR) gene expression cassette and three packaging plasmids expressing the structural HIV-1 gag-pol gene, accessory gene rev or viral envelope Vesicular stomatitis virus glycoprotein (VSV-G). Supernatant was collected 48 hours post-transfection and cell debris was removed by filtration through a 0.45 μm filter. The clarified viral supernatant was then concentrated by ultra-centrifugation at 10,000×g for 16-18 hours. The viral particle pellet was then resuspended in appropriate volume of culture medium.

Lentiviral vectors which may comprise either luciferase (Luc) or the NY-ESO1 T-cell receptor (NY-ESO1) and containing the WPRE, the WPRE lacking the X-fragment, or lacking the WPRE, are denoted as in table 2:

TABLE 2

A summary of lentiviral vector produced using various transgene plasmids

| Lentiviral vector ID | Transgene | WPRE or Stuffer sequence |
|---|---|---|
| Luc | luciferase | Full length WPRE |
| LucNoW 0 mer | luciferase | WPRE removed |
| LucNoW 3 mer | luciferase | WPRE replaced by 3-mer (TCT) sequence |
| LucNoW 6 mer | luciferase | WPRE replaced by 6-mer (TCTAGA) sequence |
| LucNoW 10 mer | luciferase | WPRE replaced by 10-mer (GCAACTAGAA) sequence |
| LucNoW 20 mer | luciferase | WPRE replaced by 20-mer (ACCAAGCTGG ACATCTACCC) sequence |
| LucNoW 30 mer | luciferase | WPRE replaced by 30-mer (CCGAAGGAGT ACTATAAACC GCCATACGGA) sequence |
| LucNoW 40 mer | luciferase | WPRE replaced by 40-mer (GGCGAGTTTA AAACCTCTTG CTACATCGCC TCATCTGTGA) sequence |

TABLE 2-continued

A summary of lentiviral vector produced using various transgene plasmids

| Lentiviral vector ID | Transgene | WPRE or Stuffer sequence |
|---|---|---|
| LucNoW 50 mer | luciferase | WPRE replaced by 50-mer (GTGACGAACA TGGGGCAGAT TGCTTCCAGT GCTTGCTGGG CATTGCTGAT) sequence |
| NY-ESO1 WPRE | NYESO-1 TCR | Full length WPRE |
| NY-ESO1 WPRE NoX | NYESO-1 TCR | truncated WPRE - X-promoter & partial X-protein at the 3'-end removed |
| NY-ESO1 NoW 6 mer | NYESO-1 TCR | WPRE replace by 6-mer (TCTAGA) sequence |

Lentiviral Vector Transduction of Target Cells—SupT1 Cell Line

The expression of the luciferase reporter gene or NYESO-1 TCR in target cells was evaluated by transducing a human SupT1 cell line. For the transduction, SupT1 cells were pelleted and were resuspended in fresh culture medium. These cells were seeded at a density of 1×10^6 cell/well at 0.5 ml per well in a 24-well plate. Then 0.5 ml of lentiviral vector was added to the well.

Transduced SupT1 cells were harvested as cell pellets [300×g for 5 minutes] for the measurement of luciferase expression 48 hours later. For the measurement of NYESO-1 TCR, these cells were stained with a specific antibody raised against the beta-chain of the TCR and the % of positively labelled cells was determined by flow cytometry.

Expression of Active Luciferase in Sup T Cells Transduced with Lentiviral Vector Derived from Luciferase Expressing Transgene Plasmids Containing Fill Length WPRE or WPRE Replacing Stuffer Sequences.

SupT1 cell pellets were incubated with appropriate amount of cold Glo Lysis Buffer (Promega E2661) on ice for >5 minutes after vigorous vortexing for 1 min. The cell lysates were then kept on ice until use. A luciferase standard curve was generated using appropriate amount of Quanti-Lum recombinant Luciferase (Promega E1701) diluted in Glo Lysis buffer Then appropriate amount of standards and samples were added to the wells of a solid-wall white 96-well plate (Greiner Bio Cat #655083). For each well 100 μl of reconstituted Bright-Glo™ Luciferase Assay Substrate (Promega E2620) equilibrated to room temperature were added. The luminescence (relative light unit, RLU) of each well corresponding to the level of luciferase expression was measured by FLUOStar Omega plate reader (BMG LabTech). The luminescence of each sample well was converted to the concentration of active luciferase in ng/ml using the standard curve.

Figure 11:
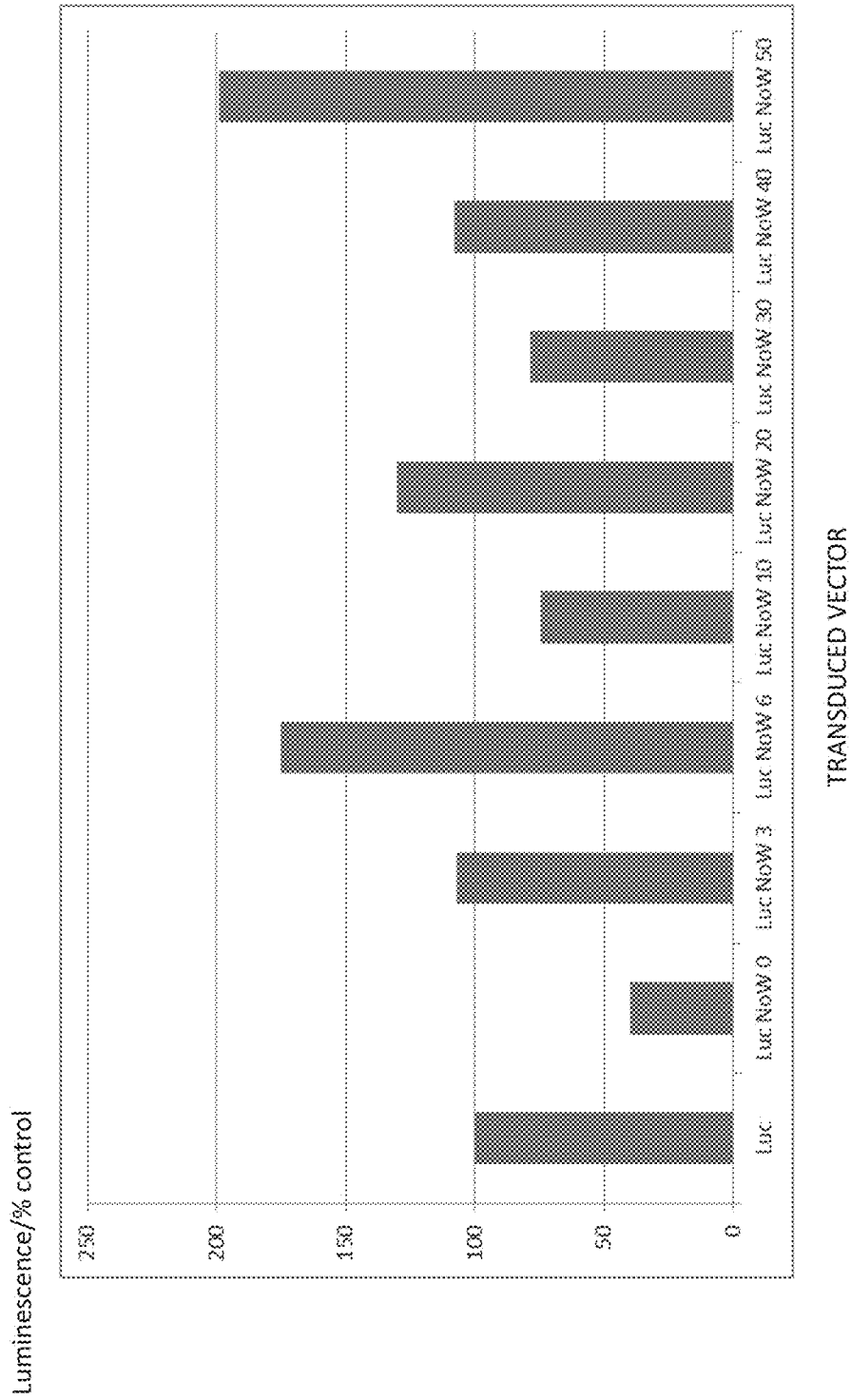
FIG. 11 is a graph showing the luciferase activities expressed by SupT1 cells transduced with LV derived from luciferase expressing transgene plasmids containing full length WPRE or WPRE replacing stuffer sequences.

Four individual lentiviral vector preps were made for each transgene plasmid. The results in fig 11 are from a typical prep and represents the mean of triplicate determinations, normalised to give the luminescence of the Luc vector as 100%. The expression of the transgene is significantly reduced in the absence of the WPRE, but this expression can be restored by the addition of a "stuffer sequence" of from 3 to 50 nucleotides.

Expression of NYESO-1 TCR on Cell Surface of SupT1 Cells Transduced with NY-ESO1 WPRE NoX or NY-ESO1 NoW 6 mer To evaluate whether similar results could be obtained with lentiviral vector expressing the NYESO-1 T-cell receptor gene (Robbins et al [2008]J Immunol 180:9, 611), some SupT1 cells were transduced with lentiviral vector derived from NY ESO-1 expressing transgene plasmid containing either a truncated WPRE NYESO1 WPRE NoX or WPRE replaced by the 6 nucleotide [TCTAGA] sequence NY-ESO1 NoW 6 mer.

Following the transduction culture medium of the SupT1 cells was replaced by FACS buffer [PBS, pH 7.4, without calcium & magnesium supplemented with 2% FBS and 2 mM EDTA] containing 13.1β PE conjugated antibody (Beckman Coulter IM2292) raised against the V3 subunit of NYESO-1 TCR diluted to 1 μl per well for a 96-well plate. The % of positively labelled cells in the population was then determined by flow cytometry using an Accuri C6 Flow Cytometer (BD BioSciences).

Figure 12:
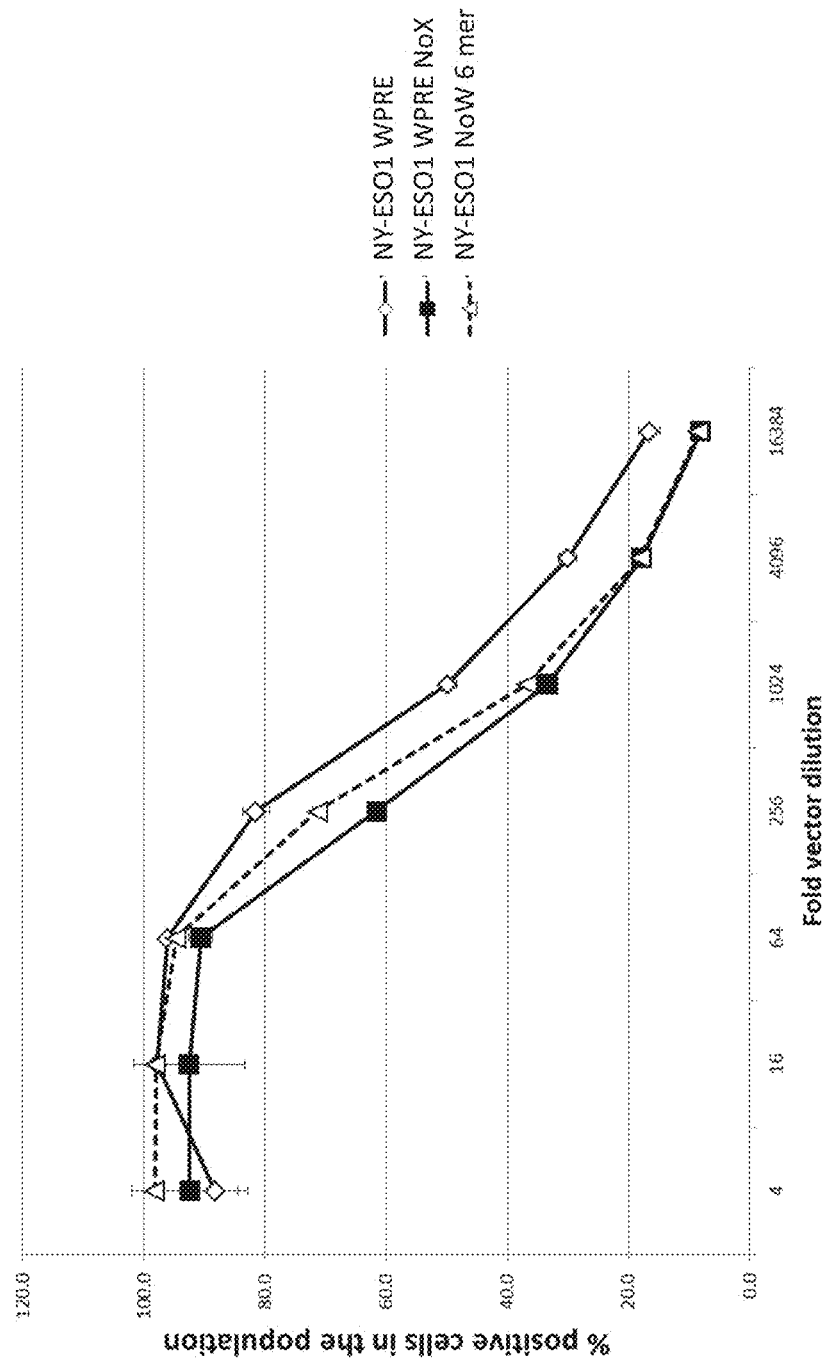
FIG. 12 shows expression of the NYESO-1 TCR on the surface of SupT1 cells transduced with serial dilutions of NY-ESO1, NY-ESO1 WPRE NoX or NY-ESO1 NoW 6 mer.

Results as shown in FIG. 12 shows that cells transduced with a vector containing a stuffer sequence (NYESO1 NoW 6 mer) were able to yield similar percentage of NYESO1 TCR expressing cells as the cells transduced with the vector containing the WPRE (NYESO1 WPRE NoX).

The Invention is Further Described by the Following Numbered Paragraphs:

1. An engineered or non-naturally occurring retroviral vector comprising a spacer or stuffer nucleotide sequence (SNS) inserted in place of a woodchuck hepatitis virus post-transcriptional regulatory element (WPRE), wherein the SNS is heterologous to the vector and does not include a start codon.

2. An engineered or non-naturally occurring retroviral vector containing and expressing a nucleotide sequence of interest (NOI) and a spacer or stuffer nucleotide sequence (SNS) for stimulation of expression of the NOI, wherein the SNS is heterologous to the vector and does not include a start codon.

3. The vector of paragraph 2, wherein the vector does not contain a woodchuck hepatitis virus post-transcriptional regulatory element (WPRE).

4. The vector of paragraphs 1 or 3, wherein the WPRE contains an X region

5. The vector of any one of paragraphs 1-4, wherein the SNS is about three to about fifty nucleotides in length.

6. The vector of any one of paragraphs 1-4 wherein the SNS is about three to about ten nucleotides in length.

7. The vector of any one of paragraphs 1-4 wherein the SNS comprises the sequence of SEQ ID NO: 1.

8. The vector of any one of paragraphs 1 or 4-7, wherein the vector comprises at least one nucleotide sequence of interest (NOI).

9. The vector of any one of paragraphs 1-8, wherein the vector is a lentiviral vector.

10. The vector of paragraph 9, wherein the lentiviral vector is a minimal lentiviral vector.

11. The vector of paragraph 9 or 10, wherein the lentiviral vector is derived from a viral species selected from the group consisting of human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), and bovine immunodeficiency virus (BIV).

12. The vector of any one of paragraphs 1-11, wherein a nucleic acid sequence encoding Rev is disrupted such that the nucleic acid sequence encodes a non-functional Rev.

13. The vector of any one of paragraphs 1-12, wherein a nucleic acid sequence encoding Tat is disrupted such that the nucleic acid sequence encodes a non-functional Tat.

14. The vector of any one of paragraphs 1-13, wherein the vector comprises a central polypurine tract (cPPT) sequence.

15. The vector of any one of paragraphs 1-14, wherein the vector comprises a gag-packaging signal comprising an ATG motif.

16. The vector of paragraph 15, wherein the ATG motif is an ATTG motif.

17. The vector of any one of paragraphs 1-16, wherein the vector is multicistronic.

18. The vector of any one of paragraphs 1-17, wherein the vector comprises at least one internal regulatory element.

19. The vector of paragraph 18, wherein the internal regulatory element is a promoter.

20. The vector of paragraph 18 or 19, wherein the internal regulatory element is an internal ribosomal entry site (IRES).

21. A retroviral vector system for producing a retrovirus-derived vector particle comprising (i) the vector of any one of paragraphs 1-20, (ii) a nucleotide sequence encoding retroviral gag and pol proteins and (iii) nucleotide sequences encoding other essential viral packaging components not encoded by the nucleotide sequence of (ii).

22. The system of paragraph 21, wherein a nucleic acid sequence(s) encoding at least one of Vpr, Vif, Tat, Nef, or analogous auxiliary proteins are disrupted such as said nucleic acid sequence(s) encode non-functional Vpr, Vif, Tat, Nef, or analogous auxiliary proteins.

23. The system of paragraph 21 or 22, wherein the vector system is pseudotyped with at least part of a heterologous env protein.

24. The system of paragraph 23, wherein the heterologous env protein is derived from Rabies-G or VSV-G.

25. The viral particle produced from the system of any one of paragraphs 21-24.

26. A cell transduced with the system of any one of paragraphs 21-24.

27. A composition comprising the vector, system, particle or cell of any one of paragraphs 1-26 and a carrier or diluent.

28. A method for delivering at least one NOI to a target cell comprising introducing the vector of any one of paragraphs 1-21 into a target cell thereby delivering the NOI to the target cell.

29. A method of enhancing transcription of a NOI in a retroviral or lentiviral expression vector comprising introducing a SNS inserted in place of a WPRE downstream of the NOI, wherein the expression of the NOI is higher when the SNS is inserted in place of the WPRE as compared to the WPRE.

30. The method of paragraph 29 wherein the WPRE contains an X region

31. The method of paragraph 29 or 30 wherein the SNS is about three to about fifty nucleotides in length.

32. The method of paragraph 29 or 30 wherein the SNS is about three to about ten nucleotides in length.

33. The method of paragraph 29 or 30 wherein the SNS comprises the sequence of any one of SEQ ID NO:s 1 to 7

34. The method of any one of paragraphs 29-33, wherein the vector is a lentiviral vector.

35. The method of paragraph 34, wherein the lentiviral vector is a minimal lentiviral vector.

36. The method of paragraph 34, wherein the lentiviral vector is derived from a viral species selected from the group consisting of human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), and bovine immunodeficiency virus (BIV).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An engineered or non-naturally occurring lentiviral vector comprising a spacer or stuffer nucleotide sequence (SNS) inserted in place of a woodchuck hepatitis virus post-transcriptional regulatory element (WPRE), wherein the SNS is heterologous to the vector and does not include a start codon and wherein the SNS is about three to about fifty nucleotides in length.

2. An engineered or non-naturally occurring lentiviral vector containing and expressing a nucleotide sequence of interest (NOI) and a spacer or stuffer nucleotide sequence (SNS) for stimulation of expression of the NOI, wherein the SNS is heterologous to the vector and does not include a start codon, wherein the vector does not contain a woodchuck hepatitis virus post-transcriptional regulatory element (WPRE) and wherein the SNS is about three to about fifty nucleotides in length.

3. The vector of claim 1 wherein the SNS is about three to about ten nucleotides in length.

4. The vector of claim 1 wherein the SNS comprises the sequence of SEQ ID NO: 1.

5. The vector of claim 1, wherein the vector comprises at least one nucleotide sequence of interest (NOI).

6. The vector of claim 1, wherein the lentiviral vector is a minimal lentiviral vector.

7. The vector of claim 1, wherein the lentiviral vector is derived from a viral species selected from the group consisting of human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), and bovine immunodeficiency virus (BIV).

8. The vector of claim 1, wherein a nucleic acid sequence encoding Rev is disrupted such that the nucleic acid sequence encodes a non-functional Rev.

9. The vector of claim 1, wherein a nucleic acid sequence encoding Tat is disrupted such that the nucleic acid sequence encodes a non-functional Tat.

10. The vector of claim 1, wherein the vector comprises a central polypurine tract (cPPT) sequence.

11. The vector of claim 1, wherein the vector comprises a gag-packaging signal comprising an ATG motif.

12. The vector of claim 11, wherein the ATG motif is an ATTG motif.

13. The vector of claim 1, wherein the vector is multicistronic.

14. The vector of claim 1, wherein the vector comprises at least one internal regulatory element.

15. The vector of claim 14, wherein the internal regulatory element is a promoter or an internal ribosomal entry site (IRES).

16. The vector of claim 1 wherein the SNS is about three to about fourteen nucleotides in length.

17. The vector of claim 1 wherein the SNS is about three to about twelve nucleotides in length.

18. The vector of claim 1 wherein the SNS is about three to about nine nucleotides in length.

19. The vector of claim 1 wherein the SNS is about three to about eight nucleotides in length.

20. The vector of claim 1 wherein the SNS is about three to about seven nucleotides in length.

21. The vector of claim 1 wherein the SNS is about three to about five nucleotides in length.

* * * * *

```
                              SEQUENCE LISTING

<160> NUMBER OF SEQ ID NOS: 19

<210> SEQ ID NO 1
<211> LENGTH: 6
<212> TYPE: DNA
<213> ORGANISM: Artificial Sequence
<220> FEATURE:
<223> OTHER INFORMATION: Oligonucleotide

<400> SEQUENCE: 1 tctaga                                                                    6

<210> SEQ ID NO 2
<211> LENGTH: 3
<212> TYPE: DNA
<213> ORGANISM: Artificial Sequence
<220> FEATURE:
<223> OTHER INFORMATION: Oligonucleotide

<400> SEQUENCE: 2 tct                                                                       3

<210> SEQ ID NO 3
<211> LENGTH: 10
<212> TYPE: DNA
<213> ORGANISM: Artificial Sequence
<220> FEATURE:
<223> OTHER INFORMATION: Oligonucleotide

<400> SEQUENCE: 3
gcaactagaa                                                               10

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
accaagctgg acatctaccc                                                    20

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide

<400> SEQUENCE: 5
ccgaaggagt actataaacc gccatacgga                                         30

<210> SEQ ID NO 6
<211> LENGTH: 40
<212> TYPE: DNA
<213> ORGANISM: Artificial Sequence
<220> FEATURE:
<223> OTHER INFORMATION: Oligonucleotide

<400> SEQUENCE: 6
ggcgagttta aaacctcttg ctacatcgcc tcatctgtga                              40
```

<210> SEQ ID NO 7
<211> LENGTH: 50
<212> TYPE: DNA
<213> ORGANISM: Artificial Sequence
<220> FEATURE:
<223> OTHER INFORMATION: Oligonucleotide

<400> SEQUENCE: 7
gtgacgaaca tggggcagat tgcttccagt gcttgctggg cattgctgat          50

<210> SEQ ID NO 8
<211> LENGTH: 9
<212> TYPE: DNA
<213> ORGANISM: Artificial Sequence
<220> FEATURE:
<223> OTHER INFORMATION: Oligonucleotide

<400> SEQUENCE: 8 tcgactctg                                                        9

<210> SEQ ID NO 9
<211> LENGTH: 9
<212> TYPE: DNA
<213> ORGANISM: Artificial Sequence
<220> FEATURE:
<223> OTHER INFORMATION: Oligonucleotide

<400> SEQUENCE: 9 aattcagag                                                        9

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide

<400> SEQUENCE: 10
tcgacgcaac tagaag                                               16

<210> SEQ ID NO 11
<211> LENGTH: 16
<212> TYPE: DNA
<213> ORGANISM: Artificial Sequence
<220> FEATURE:
<223> OTHER INFORMATION: Oligonucleotide

<400> SEQUENCE: 11
aattcttcta gttgcg                                               16

<210> SEQ ID NO 12
<211> LENGTH: 26
<212> TYPE: DNA
<213> ORGANISM: Artificial Sequence
<220> FEATURE:
<223> OTHER INFORMATION: Oligonucleotide

<400> SEQUENCE: 12
tcgacaccaa gctggacatc tacccg                                    26

<210> SEQ ID NO 13
<211> LENGTH: 26
<212> TYPE: DNA
<213> ORGANISM: Artificial Sequence
<220> FEATURE:

```
<223> OTHER INFORMATION: Oligonucleotide

<400> SEQUENCE: 13
aattcgggta gatgtccagc ttggtg                                         26

<210> SEQ ID NO 14
<211> LENGTH: 36
<212> TYPE: DNA
<213> ORGANISM: Artificial Sequence
<220> FEATURE:
<223> OTHER INFORMATION: Oligonucleotide

<400> SEQUENCE: 14
tcgacccgaa ggagtactat aaaccgccat acggag                              36

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide

<400> SEQUENCE: 15
aattctccgt atggcggttt atagtactcc ttcggg                              36

<210> SEQ ID NO 16
<211> LENGTH: 46
<212> TYPE: DNA
<213> ORGANISM: Artificial Sequence
<220> FEATURE:
<223> OTHER INFORMATION: Oligonucleotide

<400> SEQUENCE: 16
tcgacggcga gtttaaaacc tcttgctaca tcgcctcatc tgtgag                   46

<210> SEQ ID NO 17
<211> LENGTH: 46
<212> TYPE: DNA
<213> ORGANISM: Artificial Sequence
<220> FEATURE:
<223> OTHER INFORMATION: Oligonucleotide

<400> SEQUENCE: 17
aattctcaca gatgaggcga tgtagcaaga ggttttaaac tcgccg                   46

<210> SEQ ID NO 18
<211> LENGTH: 56
<212> TYPE: DNA
<213> ORGANISM: Artificial Sequence
<220> FEATURE:
<223> OTHER INFORMATION: Oligonucleotide

<400> SEQUENCE: 18
tcgacgtgac gaacatgggg cagattgctt ccagtgcttg ctgggcattg ctgatg        56

<210> SEQ ID NO 19
<211> LENGTH: 56
<212> TYPE: DNA
<213> ORGANISM: Artificial Sequence
<220> FEATURE:
<223> OTHER INFORMATION: Oligonucleotide

<400> SEQUENCE: 19
aattcatcag caatgcccag caagcactgg aagcaatctg ccccatgttc gtcacg        56
```